United States Patent [19]
Bacon et al.

[11] Patent Number: 5,977,118
[45] Date of Patent: Nov. 2, 1999

[54] 6-SUBSTITUTED PYRAZOLO[3,4-D] PYRIMIDIN-4-ONES AND COMPOSITIONS AND METHODS OF USE THEREOF

[75] Inventors: Edward R. Bacon, Audubon, Pa.; Sol J. Daum, Albany, N.Y.; Baldev Singh, Collegeville, Pa.

[73] Assignee: Sanofi, Paris, France

[21] Appl. No.: 08/824,600

[22] Filed: Mar. 26, 1997

Related U.S. Application Data

[62] Division of application No. 08/402,268, Mar. 10, 1995, Pat. No. 5,656,629.

[51] Int. Cl.$^6$ ........................ A61K 31/505; C07D 487/04
[52] U.S. Cl. ............................................ 514/258; 544/262
[58] Field of Search .............................. 514/234.5, 237.2, 514/258; 544/262, 116, 126

[56] References Cited

U.S. PATENT DOCUMENTS

| | | | |
|---|---|---|---|
| 3,211,731 | 10/1965 | Schmidt et al. | 544/262 |
| 3,716,555 | 2/1973 | Howarth et al. | 544/262 |
| 3,821,282 | 6/1974 | Hoyle et al. | 544/262 |

FOREIGN PATENT DOCUMENTS

| | | | |
|---|---|---|---|
| 0525004A1 | 2/1993 | European Pat. Off. | 487/4 |
| WO93/07149 | 4/1993 | WIPO | 487/4 |
| WO94/00453 | 1/1994 | WIPO | 473/30 |

OTHER PUBLICATIONS

Silver et al. "Cyclic GMP Potentiation by WIN 58237, a Novel Cyclic Nucleotide . . . " *J. Pharm. Exp. Ther.* 271, 1143–1148 (1994).

*Primary Examiner*—John M. Ford
*Attorney, Agent, or Firm*—Michael D. Alexander; Paul E. Dupont

[57] ABSTRACT

6-Substituted pyrazolo[3,4-d]pyrimidin-4-one derivatives, pharmaceutical compositions containing them and methods for effecting c-GMP-phosphodiesterase inhibition and for treating heart failure and/or hypertension.

21 Claims, No Drawings

6-SUBSTITUTED PYRAZOLO[3,4-D] PYRIMIDIN-4-ONES AND COMPOSITIONS AND METHODS OF USE THEREOF

This application is a division of application Ser. No. 08/402,268 filed on Mar. 10, 1995 now U.S. Pat. No. 5,656,629.

BACKGROUND OF THE INVENTION (a) Field of the Invention

The invention relates to 6-substituted pyrazolo[3,4-d]-pyrimidin-4-ones, to pharmaceutical compositions containing them and to methods for effecting c-GMP-phosphodiesterase inhibition and for treating heart failure and/or hypertension.

(b) Information Disclosure Statement

Schmidt et al., U.S. Pat. No. 3,165,520, issued Jan. 12, 1965, disclose as coronary dilating agents pyrazolo-[3,4-d] pyrimidines of general formula:

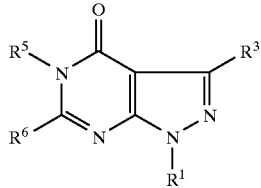

wherein:

$R^1$ represents a hydrogen atom or an alkyl, hydroxyalkyl, halogen-alkyl or oxa-alkyl radical or a cycloalkyl, cycloalkyl-alkyl, aralkyl or heterocyclylalkyl radical or an at most binuclear aryl or heterocyclic radical;

$R^3$ represents a hydrogen atom or a lower-alkyl radical;

$R^5$ represents an aliphatic, cycloaliphatic, cycloaliphatic-aliphatic, araliphatic or heterocyclic-aliphatic radical; and $R^6$ represents an aliphatic radical or an aralkyl or heterocyclyl-alkyl radical which may be substituted.

The patent more specifically discloses as especially valuable the compounds in which $R^1$ represents a hydrogen atom or a lower-alkyl radical or a cycloalkyl radical, a hydroxy-lower-alkyl radical or halogen-lower-alkyl radical, an oxa-lower-alkyl, or an aryl radical which may be unsubstituted or mono-, di-, or tri-substituted by halogen, alkoxy, alkyl, methylenedioxy, trifluoromethyl, nitro, amino, or a pyridyl radical; $R^3$ represents a hydrogen atom or a lower-alkyl radical; $R^5$ represents a lower-alkyl radical or a lower-alkylamino radical; and $R^6$ represents a lower-alkyl radical or an aralkyl radical.

Further disclosed are a series of $1-R^1-3-R^3-4$-hydroxy-6-$R^6$-pyrazolo[3,4-d]pyrimidines which are said to be useful as intermediates in the synthesis of final products. Among the intermediates specifically disclosed are 1-cyclopentyl-4-hydroxy-6-benzyl-pyrazolo[3,4-d]pyrimidine and 1-isopropyl-4-hydroxy-6-m-methoxybenzylpyrazolo[3,4-d]pyrimidine.

Schmidt et al., U.S. Pat. No. 3,211,731, issued Oct. 12, 1965, disclose as coronary dilating agents pyrazolo-[3,4-d] pyrimidines of general formula:

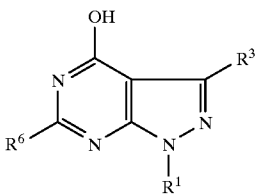

wherein:

$R^1$ represents hydrogen, an alkyl, hydroxy-alkyl, halogen-alkyl or oxa-alkyl radical, a cyclo-alkyl, cycloalkylalkyl, aralkyl, heterocyclyl-alkyl radical or an at most binuclear aryl or heterocyclic radical;

$R^3$ stands for hydrogen, or in the second place, for a lower-alkyl radical; and $R^6$ represents a possibly substituted aralkyl or heterocyclylalkyl radical.

The patent more specifically discloses as especially valuable the compounds in which $R^1$ represents a hydrogen atom or a lower-alkyl group, cycloalkyl, hydroxy-lower-alkyl, halogen-lower-alkyl, oxa-lower-alkyl, or an aryl; $R^3$ represents a hydrogen atom or lower-alkyl and $R^6$ a substituted or unsubstituted aralkyl. Among the compounds specifically disclosed are 1-isopropyl-4-hydroxy-6-(3'-methoxyphenylmethyl)pyrazolo[3,4-d]pyrimidine, 1-cyclopentyl-4-hydroxy-6-benzylpyrazolo[3,4-d] pyrimidine, 1-iso-propyl-4-hydroxy-6-(β-phenylethyl) pyrazolo[3,4-d]pyrimidine, and 1-isopropyl-4-hydroxy-6-(4-aminobenzyl)pyrazolo[3,4-d]pyrimidine.

Schmidt et al., U.S. Pat. No. 3,211,732, issued Oct. 12, 1965, disclose, as intermediates, $1-R^1-3-R^3-6-R^6-4$-hydroxy-pyrazolo[3,4-d]pyrimidines wherein:

$R^1$ represents a hydrogen atom, a lower-alkyl radical which is unsubstituted or substituted by a hydroxy group or a lower-alkoxy group, or a cyclopentyl or cyclohexyl radical or a phenyl or phenyl lower-alkyl radical;

$R^3$ represents a hydrogen atom or a lower-alkyl radical; and $R^6$ stands for a substituted or unsubstituted phenyl lower-alkyl radical.

Specifically disclosed is 1-isopropyl-4-hydroxy-6-benzylpyrazolo[3,4-d]pyrimidine.

Also disclosed, as intermediates, are $1-R^1-3-R^3-6-R^6-4$-hydroxypyrazolo[3,4-d]pyrimidines wherein:

$R^1$ stands for a hydrogen atom, a lower-alkoxy-lower-alkyl radical or a hydroxy-lower-alkyl radical, a cyclopentyl or cyclohexyl radical or a phenyl or phenyl-lower-alkyl radical which may be substituted;

$R^3$ has the meanings given above; and $R^6$ stands for a phenyl radical which may be substituted. Specifically disclosed is 1-isopropyl-4-hydroxy-6-phenylpyrazolo-[3,4-d]pyrimidine.

Breuer et al., U.S. Pat. No. 3,732,225, issued May 8, 1973, disclose as hypoglycemic agents and anti-inflammatory agents pyrazolo[3,4-d]pyrimidines of formula:

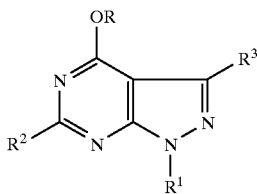

wherein:
R is hydrogen or lower-alkyl; $R^1$ is lower-alkyl, cycloalkyl, phenyl or substituted phenyl; $R^2$ is phenyl, substituted phenyl or cycloalkyl; and $R^3$ is hydrogen, lower-alkyl, cycloalkyl, phenyl or substituted phenyl. Specifically disclosed are 1-methyl-6-phenyl and 1-methyl-6-(4-chlorophenyl)pyrazolo[3,4-d]pyrimidin-4-ones.

Burch, U.S. Pat. No. 3,350,397, issued Oct. 31, 1967, discloses as antibacterial agents pyrazolo[3,4-d]pyrimidines of formula:

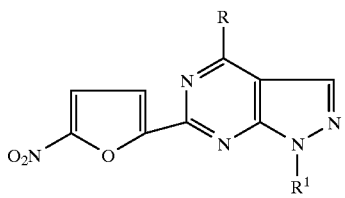

wherein:
R represents a member of the group consisting of hydroxy, chloro and —N(X) (Y) wherein X represents a member of the group consisting of hydrogen, (lower) alkyl, hydroxy(lower)alkyl, (lower)alkoxy(lower)alkyl and amino; Y represents a member of the group consisting of hydrogen, hydroxy(lower)alkyl, (lower)alkoxy(lower)alkyl and morpholinopropyl; X and Y taken together with N represent pyrrolidyl; and $R^1$ represents a member of the group consisting of (lower) alkyl and methoxyethyl.

The patent further discloses, as intermediates, 4-amino and 4-hydroxy-1-$R^1$-6-(2-furyl)-1H-pyrazolo[3,4-d] pyrimidines. The preparation of intermediates and the preparation and biological testing of final products is further exemplified by Burch in J. Med. Chem. 1968, 11, 79.

British Patent 937,722, published Sep. 25, 1963, to CIBA LIMITED, discloses as a coronary dilating agent 1-isopropyl-4-hydroxy-6-benzyl-pyrazolo[3,4-d] pyrimidine.

Hamilton, U.S. Pat. No. 4,666,908, issued May 19, 1987, discloses pyrazolo[4,3-d]pyrimidine-7-ones of formula:

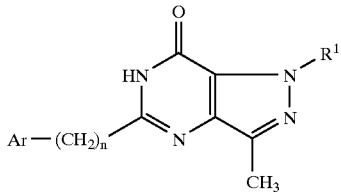

wherein:
$R^1$ is lower-alkyl of from one to six carbons, inclusive, lower-alkylene of from one to six carbon, inclusive, lower-hydroxyalkyl of from one to six carbons, inclusive, lower-hydroxyalkylene of from two to six carbons, inclusive, lower-aminoalkyl of from one to six carbons, inclusive, or lower-aminoalkylene of from two to six carbons, inclusive;
n is 0–4; and
Ar is $R_2$:

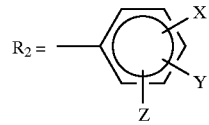

or 2, 3 or 4-pyridyl wherein X, Y and Z are independently (1) hydrogen; (2) lower-alkyl of from one to six carbons, inclusive; (3) halogen; (4) hydroxyl; (5) lower-alkoxy of from one to six carbons, inclusive; (6) nitro; (7) amino; (8) NR'R" wherein R' and R" are each independently (a) hydrogen or (b) lower-alkyl of from one to six carbons, inclusive, optionally substituted by (i) amino, (ii) morpholino, or (iii) cycloalkyl of from five to seven carbons, inclusive, (9) sulfonyl or (10) —SO2 NR'R" wherein R' and R" are as defined above.

The patent more specifically discloses as preferred compounds those wherein Ar is $R_2$. The compounds are stated to be useful in the treatment of cardiovascular disorders.

Miyashita et al., Heterocycles 1990, 31, 1309–1314, describe the preparation of a series of pyrazolo[3,4-d] pyrimidines of general formula:

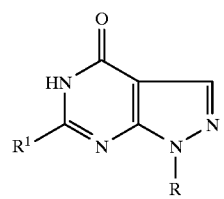

wherein:
R is phenyl or methyl; and $R^1$ is hydrogen, methyl, ethyl, propyl, isopropyl, benzyl, ethyl carboxylate or phenyl. No indication of utility is disclosed.

Hamilton, PCT Application WO 88/00192, published Jan. 14, 1988, discloses a series of 5-substituted pyrazolo[4,3-d] pyrimidin-7-one derivatives which are stated to be useful as cardiotonic, CNS stimulative, antiallergy, antiasthma or cognition activating agents.

Bell et al., European Patent Application 0463756, published Jan. 2, 1992, disclose a series of 5-(2,5-disubstituted-phenyl)pyrazolo[4,3-d]pyrimidin-7-ones which are stated to be useful in the treatment of cardiovascular disorders.

Breuer and Treuner, U.S. Pat. No. 3,847,908, issued Nov. 12, 1974, disclose compounds of the formula:

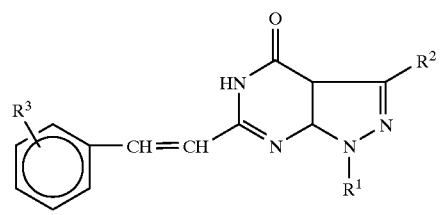

wherein:
$R^1$ is lower-alkyl, cyclolower-alkyl, or phenyl-lower-alkyl;

R[2] is hydrogen or lower-alkyl; and

R[3] is hydrogen, lower-alkyl, halogen, or trifluoromethyl. Specifically disclosed are 1,3-dimethyl-6-styryl-pyrazolo[3,4-d]pyrimidine, 1-cyclopentyl-6-(2-chlorostyryl)pyrazolo[3,4-d]pyrimidine, 1-cyclohexyl-3-methyl-6-(styryl)pyrazolo[3,4-d]pyrimidine and 1,3-diethyl-6-(4-chlorostyryl)pyrazolo[3,4-d]pyrimidine. The compounds are said to be useful as antimicrobial agents and to possess antiinflammatory and membrane stabilizing properties.

Morrison et al., U.S. Pat. No. 4,260,758, issued Apr. 7, 1981, disclose the preparation of compounds of the formula:

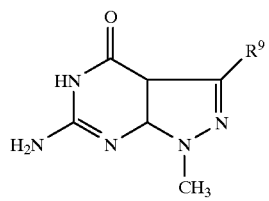

wherein R[9] is selected from lower-alkyl, phenyl, phenyl substituted by one or more hydroxy or lower-alkoxy, or pyridyl. No utility is disclosed for the compounds.

Burch, Canadian Patent 754,565, issued Mar. 14, 1967, discloses a series of 4-substituted-1-alkyl-6-(2-furyl)-1H-pyrazolo[3,4-d]pyrimidines which are said to be useful as intermediates in the preparation of 4-substituted-1-alkyl-6-(5-nitro-2-furyl)-1H-pyrazolo[3,4-d]pyrimidines which are said to inhibit bacterial growth.

Podesva et al., U.S. Pat. No. 3,772,294, issued Nov. 13, 1973, disclose a process for preparing compounds of the formula I:

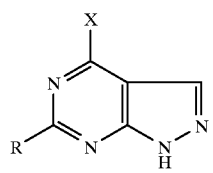

wherein:

X represents a halogen atom, a free or substituted hydroxyl, amino or mercapto group and R represents a hydrogen atom, or a lower-alkyl or a substituted or unsubstituted aryl radical. The compounds are disclosed as being potentially useful in the treatment of hyperuricemia associated with gout and other conditions and additionally, the compounds wherein X represents a halogen atom are said to be useful as intermediates in the synthesis of other compounds having the formula I. Specifically disclosed is 4-hydroxy-6-phenyl-1-pyrazolo[3,4-d]pyrimidine.

Coates and Rawlings, U.S. Pat. No. 5,075,310, issued Dec. 24, 1991 from application Ser. No. 370,494 filed Jun. 23, 1989, disclose and claim compounds of the formula:

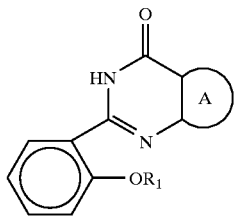

and pharmaceutically acceptable salts thereof, wherein:

is a ring of sub-formula (a), (b) or (c):

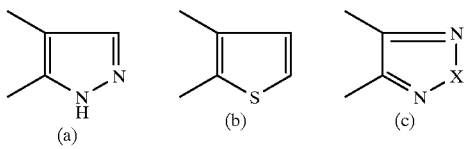

X is oxygen or sulphur; and

R[1] is $C_1$–$C_6$ alkyl, $C_{2-6}$ alkenyl, $C_{3-5}$ cycloalkyl—$C_{1-4}$ alkyl, or $C_{1-4}$ alkyl substituted by 1 to 6 fluoro groups. Specifically disclosed is 6-(2-propoxyphenyl)pyrazolo [3,4-d]pyrimidin-4(5H)-one. The compounds are said to be useful as bronchodilators and vasodilators.

Bacon et al, U.S. Pat. No. 5,294,612 issued Mar. 15, 1994 from Application Ser. No. 859,770 filed Mar. 30, 1992, discloses a series of 6-heterocyclyl-pyrazolo[3,4-d]pyrimidin-4-ones, e.g., 1-cyclopentyl-3-ethyl-6-(3-pyridyl)pyrazolo[3,4-d]pyrimidin-4-one. The compounds are disclosed to be useful in treating heart failure and hypertension.

SUMMARY OF THE INVENTION

The invention relates to compounds of the Formula I:

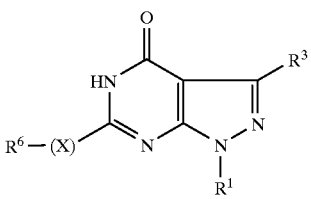

wherein:

R[1] is tert-butyl, or cyclopentyl;

R[3] is methyl, ethyl, or phenylmethyl;

X is —CH$_2$—, —O—, or —NH—; and

R[6] is phenyl (or phenyl substituted by from one to three, the same or different, substituents selected from the group consisting of lower-alkoxy, hydroxy, halogen, carboxylower-alkoxy, 4-morpholinyl-lower-alkoxy, 5-tetrazolyl-lower-alkoxy, dilower-alkylamino, trifluoromethyl, nitro, amino, lower-alkylsulfonylamino, dilower-alkylamino-lower-alkylphenyl carbonyloxy, and 1-imidazolyl); or when X is —CH$_2$—, R$^6$ is additionally 2-,3-, or 4-pyridinyl, 1-pyrrolyl, 1-benzimidazolyl, 1,2,3,4-tetrahydro-2-isoquinolinyl, 1,2,3,4-tetrahydro-1-quinolinyl, hydroxy, 1-imidazolyl, 1-lower-alkyl-2-,3-,4-, or 5-pyrrolyl, 1-pyrazolyl, 3-,4-, or 5-isoxazolyl( or 3-,4-, or 5-isoxazolyl substituted on any available carbon atom thereof by lower-alkyl), 2-thienyl, or 3-thienyl; or a pharmaceutically acceptable acid-addition salt and/or hydrate thereof.

The compounds of the Formula I have been found to possess c-GmP-PDE V inhibitory activity and are thus useful in the treatment of heart failure and/or hypertension.

Preferred compounds of Formula I above are those wherein:

R$^1$, R$^3$ and X are as defined hereinabove; and

R$^6$ is phenyl (or phenyl substituted by from one to three, the same or different, substituents selected from the group consisting of lower-alkoxy, hydroxy, carboxylower-alkoxy, 4-morpholinyl-lower-alkoxy, 5-tetrazolyl-lower-alkoxy, dilower-alkylamino, trifluoromethyl, nitro, amino, lower-alkylsulfonylamino, dilower-alkylamino-lower-alkylphenyl carbonyloxy, and 1-imidazolyl); or when X is —CH$_2$—, R$^6$ is additionally 2-,3-, or 4-pyridinyl, 1-pyrrolyl, 1-benzimidazolyl, 1,2,3,4-tetrahydro-2-isoquinolinyl, 1,2,3,4-tetrahydro-1-quinolinyl, hydroxy, 1-imidazolyl, 1-lower-alkyl-2-pyrrolyl, 1-pyrazolyl, 4-isoxazolyl substituted on any available carbon atom thereof by lower-alkyl, 2-thienyl, or 3-thienyl.

Particularly preferred compounds of Formula I above are those wherein:

R$^1$, R$^3$ and X are as defined hereinabove; and

R$^6$ is phenyl (or phenyl substituted by from one to three, the same or different, substituents selected from the group consisting of methoxy, hydroxy, carboxymethoxy, 2-(4-morpholinyl)ethoxy, 1-(5-tetrazolyl)methoxy, dimethylamino, trifluoromethyl, nitro, amino, methylsulfonylamino, diethylaminomethylphenylcarbonyloxy, and 1-imidazolyl); or when X is —CH$_2$—, R$^6$ is additionally 2-,3-, or 4-pyridinyl, 1-pyrrolyl, 1-benzimidazolyl, 1,2,3,4-tetrahydro-2-isoquinolinyl, 1,2,3,4-tetrahydro-1-quinolinyl, hydroxy, 1-imidazolyl, 1-methyl-2-pyrrolyl, 1-pyrazolyl, 3,5-dimethyl-4-isoxazolyl, 2-thienyl, or 3-thienyl.

Most preferred of the compounds of Formula I above are those wherein R$^1$ is cyclopentyl; R$^3$ is ethyl; and X and R$^6$ are as defined hereinabove, e.g.:

1-cyclopentyl-3-ethyl-6-(4-methoxyphenylmethyl) pyrazolo [3,4-d]pyrimindin-4-one, 1-cyclopentyl-3-ethyl-6-(4-hydroxyphenylmethyl) pyrazolo [3,4-d]pyrimindin-4-one, 1-cyclopentyl-3-ethyl-6-(phenylmethyl)pyrazolo[3,4-d] pyrimindin-4-one, and 1-cyclopentyl-3-ethyl-6-(4-aminophenylmethyl)pyrazolo [3,4-d]pyrimindin-4-one.

The invention further relates to pharmaceutical compositions which comprise compounds of Formula I together with a pharmaceutically acceptable carrier, adjuvant, diluent, or vehicle.

The invention further relates to a method for effecting cGMP-phosphodiesterase inhibition in a mammalian organism which comprises administering to said organism an effective amount of a compound of Formula I.

The invention further relates to a method for treating heart failure and/or hypertension in a mammalian organism which comprises administering to said organism an effective amount of a compound of the Formula I.

DETAILED DESCRIPTION INCLUSIVE OF PREFERRED EMBODIMENTS

The compounds of Formula I may exist in tautomeric equilibrium with the corresponding enol form:

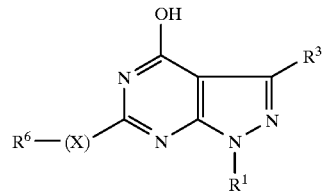

While the compounds are believed to be predominately in the keto form and will be represented as such throughout this specification, it is to be understood that the invention contemplates both forms and mixtures thereof.

The term lower-alkyl as used herein means linear or branched hydrocarbon chains having from one to about four carbon atoms and thus includes methyl, ethyl, propyl, isopropyl, n-butyl, sec-butyl, and the like.

The term lower-alkoxy as used herein means linear or branched alkyloxy substituents having from one to about four carbon atoms and thus includes methoxy, ethoxy, propoxy, isopropoxy, butoxy, sec-butoxy, and the like.

The term halogen, halide or halo as used herein means bromine, chlorine, iodine or fluorine.

The synthesis of compounds of the invention wherein X is —CH$_2$— can be outlined as shown in Scheme A:

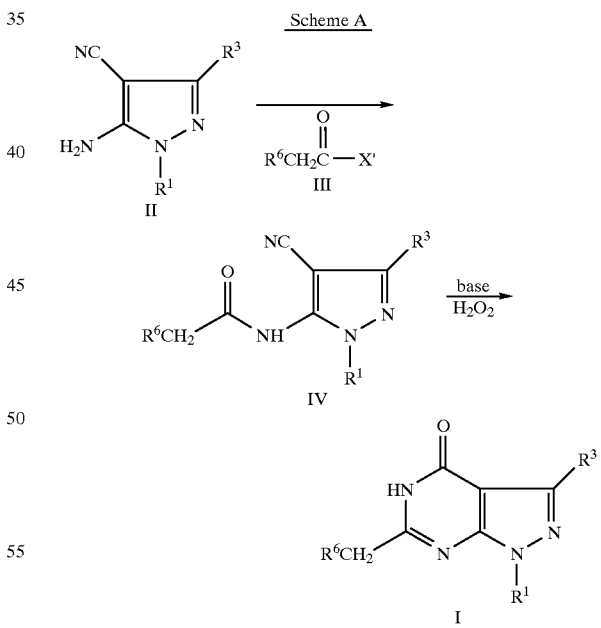

A suitably substituted 5-amino-1H-pyrazole-4-carbonitrile of the formula II in the presence of a suitable base, such as pyridine, optionally in the presence of a suitable solvent, such as chloroform, is treated with an excess of a suitably substituted acid chloride of the formula III, wherein X' is halogen, preferably chlorine, at a temperature in the range of about 0° C. up to about room temperature, to afford the carboxamides of the formula IV. Alternatively, the carboxamides of the formula IV can be prepared by treating a mixture of an excess of an acid of the formula R⁶CH₂COOH or an acid-addition salt thereof, an excess of a base, such as sodium hydride, and an excess of a suitable coupling reagent, such as N,N'-carbonyldiimidazole, in a suitable solvent, such as dimethylformamide (DMF), with a 5-amino-1H-pyrazole-4-carbonitrile of the formula II. The carboxamides of the formula IV can then be treated with an excess of hydrogen peroxide, in the presence of an excess of a base, preferably sodium hydroxide, or sodium methoxide, in a solvent such as water, a lower-alkanol, or a water/lower-alkanol mixture, preferably ethanol when sodium methoxide is used as the base, or a water/ethanol mixture when sodium hydroxide is used as the base, at a temperature in the range of about 0° C. up to the boiling point of the solvent or solvent mixture used, to afford the compounds of the formula I wherein X is —CH₂—.

Alternatively, the compounds of the formula I wherein X is —CH₂— can be prepared as shown in Scheme B:

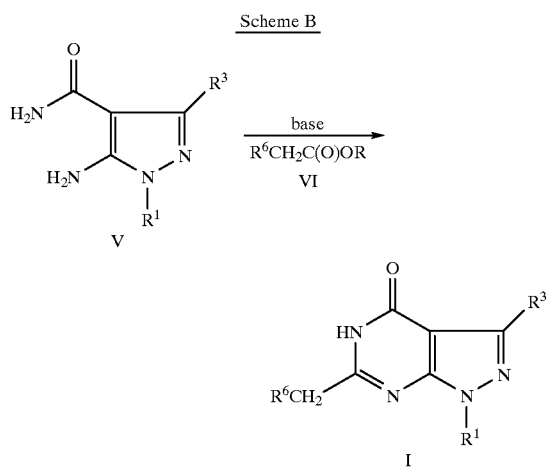

An excess of a base, such as an alkali metal lower-alkoxide, preferably sodium ethoxide, in a lower-alkanol solvent, preferably ethanol, is treated with a suitably substituted 5-amino-1H-prazole-4-carboxamide of the formula V, and an excess of a suitably substituted ester of the formula VI, wherein R is lower-alkyl, preferably methyl or ethyl, at a temperature in the range of about room temperature up to the boiling point of the solvent used, to afford the compounds of the formula I wherein X is —CH₂—.

The compounds of the formula I wherein X is —O—, or —NH—, can be prepared as shown in Scheme C:

Scheme C

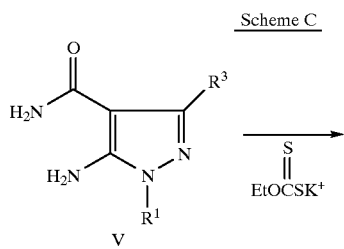

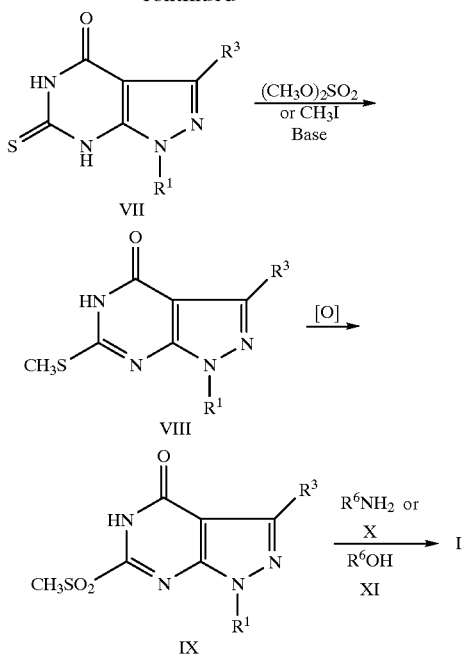

A suitably substituted 5-amino-1H-pyrazole-4-carboxamide of the formula V is treated with an excess of an o-ethylxanthic acid salt, such as the potassium salt, in a suitable organic solvent, such as N-methyl-2-pyrrolidinone, at a temperature in the range of about 80° C. up to the boiling point of the solvent used, preferably at a temperature in the range of about 150° C. to about 160° C., to afford the 6-thioxopyrazole[3,4-d]pyrimidin-4-ones of the formula VII. The compounds of the formula VII can then be treated with an excess of an appropriate methylating agent, such as methyl iodide or dimethyl sulfate, in the presence of an excess of a base, such as K₂CO₃ or sodium hydride, in a suitable organic solvent, such as dimethylformamide, at a temperature in the range of about 0° C. up to about room temperature, to afford the 6-(methylthio)pyrazole[3,4-d]pyrimidin-4-ones of the formula VIII. The compounds of the formula VIII can then be treated with an excess of a suitable oxidizing agent, such as m-chloroperoxybenzoic acid, in a suitable solvent, such as chlorofrom, at a temperature of about room temperature to afford the 6-(methylsulfonyl)pyrazolo[3,4-d]pyrimidin-4-ones of the formula IX. Treatment of the latter derivative with an excess of an R⁶NH₂ derivative of the formula X, or an excess of an R⁶OH derivative of the formula XI, optionally in the presence of an excess of a base, such as sodium hydride, at a temperature in the range of about room temperature up to about 190° C., preferably at a temperature in the range of about 170° C. to about 190° C., produces the compounds of the formula I wherein X is —O— or —NH—.

Simple chemical transformations which are conventional and well known to those skilled in the art of chemistry can be used for effecting changes in the functional groups of the compounds of the formula I. For example, dealkylation of aryl ethers to afford the corresponding phenol derivatives, treatment of aryl derivatives with formaldehyde and a dilower-alkylamine to afford the corresponding dilower-alkylaminomethyl derivatives, treatment of the compounds of the formula I wherein X is —CH₂— and R⁶ is OH with methanesulfonyl chloride in the presence of a base to afford the corresponding mesylates which in turn can be treated with 1-acetylimidazole or pyrazole to afford the compounds of the formula I wherein X is —$CH_2$— and $R^6$ is 1-imidazolyl or 1-pyrazolyl, catalytic reduction of nitro derivatives to afford the corresponding amines, sulfonylation of amines with lower-alkylsulfonyl halides to afford the corresponding lower-alkylsulfonamides, and treatment of phenols with acids in the presence of a coupling agent, e.g. N,N'-carbonyldiimidazole, to afford the corresponding esters.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The appropriately substituted 5-amino-1H-pyrazole-4-carbonitriles of the formula II and the appropriately substituted 5-amino-1H-pyrazole-4-carboxamides of the formula V are either known and thus can be prepared by procedures known in the art (see, for example, U.S. Pat. No. 5,294,612, issued Mar. 15, 1994, the entire contents of which is incorporated herein by reference), or they can be prepared by the procedures described hereinbelow in the examples. The acid chlorides of the formula III, the esters of the formula VI, the $R^6NH_2$ derivatives of the formula X and the $R^6OH$ derivatives of the formula XI, are either commercially available, or they can be prepared by procedures known in the art, or by the procedures described hereinbelow in the examples.

The structures of the compounds of the invention were established by the mode of synthesis, and by one or more of elemental analysis, and infrared, nuclear magnetic resonance and mass spectroscopy. The course of the reactions and the identity and homogenity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (°C.) and are uncorrected.

EXAMPLE 1

(a)

To a stirred solution of 1-cyclopentyl-3-ethyl-5-amino-1H-pyrazole-4-carbonitrile (8.2 g, 0.04 mol) in pyridine (100 ml) in an ice bath was added phenylacetyl chloride (10.6 ml, 0.08 mol) over a period of 20 minutes. The reaction mixture was stirred as such for 2 hours, then at room temperature overnight. The solvent was removed in vacuo, and the residue was partitioned between chloroform (200 ml) and water (200 ml). The organic layer was separated, and concentrated in vacuo to afford an oil which was purified by column chromatography on silica eluting with hexane/ether (1/1) to afford, after recrystallization from ether/hexane, 8.3 g (64%) of 1-cyclopentyl-3-ethyl-4-cyano-5-(phenylmethylcarbonylamino)-1H-pyrazole, as white flakes.

(b)

A mixture of 1-cyclopentyl-3-ethyl-4-cyano-5-(phenylmethylcarbonylamino)-1H-pyrazole (2.4 g, 7.4 mmol), ethanol (100 ml), 30% $H_2O_2$ (4.5 ml, 40 mmol), NaOH (0.3 g, 7.5 mmol) and water (10 ml) was stirred at room temperature for 1 hour, then at reflux for 1 hour. Additional 30% $H_2O_2$ (2.5 ml) was added and the mixture was refluxed for another 1 hour. The solvent was concentrated in vacuo, the residue was treated with water (25 ml) and acetic acid (3 ml) and the yellow precipitate which formed was collected by filtration, washed with water and recrystallized from isopropanol to afford 0.79 g of 1-cyclopentyl-3-ethyl-6-(phenylmethyl)-pyrazolo[3,4-d]pyrimidin-4-one, as orange needles, m.p. 175–176° C.

Alternatively, the product can be prepared as follows: sodium (2.12 g) was dissolved in ethanol (145 ml) and then 1-cyclopentyl-3-ethyl-5-amino-1H-pyrazole-4-carboxamide (10 g, 45 mmol), followed by ethyl phenylacetate (2.8 g) were added and the reaction mixture was refluxed overnight. The reaction mixture was cooled to room temperature, stripped and then water, followed by 2 N HCl were added to the residue. The product was collected by filtration and recrystallized from ethyl acetate to afford 10.52 g (73%) of 1-cyclopentyl-3-ethyl-6-(phenylmethyl)-pyrazolo[3,4-d]pyrimidin-4-one.

EXAMPLE 2

(a)

To a stirred solution of 1-cyclopentyl-3-phenylmethyl-5-amino-1H-pyrazole-4-carbonitrile (2.3 g, 8.6 mmol), $CHCl_3$ (50 ml) and pyridine (20 ml) in an ice bath was added a solution of phenylacetyl chloride (2.3 ml, 17.2 mmol) in $CHCl_3$ (10 ml) over a period of 20 minutes. The reaction mixture was stirred in an ice bath for 3 hours, then at room temperature for 2 hours. The solvent was removed in vacuo, the residue was partitioned between $CHCl_3$ (100 ml) and water (50 ml), and the organic layer was separated. Concentration of the organic layer afforded a gummy solid which was recrystallized from isopropanol to afford 1.1 g (88%) of 1-cyclopentyl-3-phenylmethyl-4-cyano-5-(phenylmethylcarbonylamino)-1H-pyrazole, as white needles, m.p. 166–168° C.

(b)

To an ice-cooled solution of 1-cyclopentyl-3-phenylmethyl-4-cyano-5-(phenylmethylcarbonylamino)-1H-pyrazole (1.1 g, 2.8 mmol) in ethanol (30 ml) was added 30% $H_2O_2$ (2.5 ml), followed by NaOH (100 mg) dissolved in water (5 ml). The reaction mixture was stirred a such for 1 hour, then at room temperature for 1 hour, then it was heated on a steam bath for 3.5 hours and finally it was stirred at room temperature overnight. The reaction mixture was concentrated to dryness, and partitioned between water (25 ml) and $CHCl_3$ (50 ml) . The organic layer was separated, and concentrated in vacuo and the oily residue was crystallized from isopropanol to afford 234 mg (22%) of 1-cyclopentyl-3-ohenylmethyl-6-(phenylmethyl)-pyrazolor[3,4-d]pyrimidin-4-one, as a white solid, m.p. 204–206° C.

EXAMPLE 3

(a)

A mixture of 1-cyclopentyl-3-ethyl-5-amino-1H-pyrazole-4-carbonitrile (4.50 g, 0.022 mol), pyridine (5.21 g, 0.066 mol), and $CHCl_3$ (75 ml) was stirred for 0.5 hours in an ice bath and then 3,4-dimethoxyphenylacetyl chloride (9.44 g, 0.044 mol) in $CHCl_3$ (25 ml) was added over 3 hours. The reaction mixture was stirred at room temperature overnight, the solvent was removed in vacuo, and the residue was partitioned between $CHCl_3$ (250 ml) and water. The layers were separated, the aqueous layer was extracted with $CHCl_3$ (2×150 ml) and the organic layers were combined and concentrated in vacuo. The residue was dissolved in $CH_2Cl_2$ (20 ml) and purified by column chromatography on silica gel eluting with ether to afford, after recrystallization from hexane/$CHCl_3$ (10/1), 1-cyclopentyl-3-ethyl-4-cyano-5-[(3,4-dimethoxyphenylmethyl)carbonyl amino]-1H-pyrazole, as white needles.

(b)

To a mixture of 1-cyclopentyl-3-ethyl-4-cyano-5-[(3,4-dimethoxyphenylmethyl)carbonylamino]-1H-pyrazole (1.0 g, 2.7 mmol), ethanol (500 ml), and $NaOCH_3$ (0.3 g) was added 30% $H_2O_2$ (4 ml). The reaction mixture was stirred at room temperature overnight, additional 30% $H_2O_2$ (3 equivalents) was added and the reaction mixture was refluxed on a steam bath for 1 hour. Starting material was still present so an additional 3 equivalents of 30% $H_2O_2$ was added and the reaction mixture was refluxed for 4 hours. The reaction mixture was stripped to dryness, treated with acetic acid and ethanol and again was stripped to dryness. The oily residue was dissolved in ethanol, water was added and the solution was cooled in an ice-bath. A solid formed which was collected by filtration and dried at 90° C. to afford 0.3 g (30%) of 1-cyclopentyl-3-ethyl-6-(3,4-dimethoxyphenylmethyl)-pyrazolo[3,4-d]pyrimidin-4-one, 1/10 hydrate, as a light yellow solid, m.p. 148–149° C.

EXAMPLE 4

(a)

To a mixture of 4-pyridine acetic acid hydrochloride (4.3 g, 25 mmol) and DMF (50 ml) cooled in an ice bath was added NaH (1.0 g, 25 mmol, 60% dispersion in mineral oil). The resulting mixture was stirred for 30 minutes and then N,N'-carbonyldiimidazole (4.0 g, 24.6 mmol) was added followed 30 minutes later by 1-cyclopentyl-3-ethyl-5-amino-1H-pyrazole-4-carbonitrile (4.1 g, 20 mmol). The reaction mixture was stirred as such for 4 hours, then at room temperature for about 2 days, and then finally was heated on a steam bath for 2 hours. The reaction mixture was concentrated to dryness and water (50 ml) and acetic acid (5 ml) were added. The mixture was extracted with $CH_2Cl_2$ (300 ml), the organic layer was concentrated in vacuo and the resulting oil was crystallized from ether and purified by column chromatography on silica gel eluting with ether to afford 2.8 g (35%) of 1-cyclopentyl-3-ethyl-4-cyano-5-[4-pyridinylmethyl) carbonylamino]-1H-pyrazole, as a viscous oil.

(b)

A mixture of 1-cyclopentyl-3-ethyl-4-cyano-5-[(4-pyridinylmethyl)carbonylamino]-1H-pyrazole (2.8 g, 8.6 mmol), ethanol (50 ml), $NaOCH_3$ (1.0 g, 18 mmol) and 30% $H_2O_2$ (4.5 ml) was stirred at room temperature for 20 minutes, then was heated at reflux for 3.5 hours. Additional 30% $H_2O_2$ (3 ml) was added and the reaction mixture was heated at reflux for 2 more hours. The reaction mixture was concentrated in vacuo, the residue was partitioned between $CHCl_3$ (100 ml) and 10% aqueous NaHCO (50 ml), and the organic layer was separated. The organic layer was concentrated in vacuo, and the residue was crystallized from cyclohexane and a solid was collected by filtration. The filtrate was concentrated in vacuo and the residue was purified by column chromatography on silica gel eluting with ether to 10% methanol/ether, followed by recrystallization from ether, to afford 420 mg of 1-cyclopentyl-3-ethyl-6-(4-pyridinylmethyl)pyrazolo[3,4-d]pyrimidin-4-one, m.p. 162–164° C.

EXAMPLE 5

To a solution of 1-cyclopentyl-3-ethyl-5-amino-1H-pyrazole-4-carboxamide (1.0 g, 4.5 mmol) in benzene (10 ml) in an ice bath was added trimethylaluminum (4.9 ml, 2M in toluene). The reaction mixture was stirred at room temperature for 1 hour, then 1-(ethoxycarbonylmethyl)pyrrole (0.7 g) in benzene (25 ml) was added and the reaction mixture was refluxed overnight. The reaction mixture was cooled, 2N HCl was added and the mixture was extracted with $CHCl_3$ (3×). The organic layer was separated, dried over $MgSO_4$, and concentrated in vacuo. The residue was digested with ether and recrystallized from ether to afford 1-cyclopentyl-3-ethyl-6-(1-pyrrolylmethyl)-pyrazolor[3,4-d]pyrimidin-4-one, m.p. 170–172° C.

EXAMPLE 6

Sodium spheres (207 mg) were dissolved in ethanol (15 ml) and 1-cyclopentyl-3-ethyl-5-amino-1H-pyrazole-4-carboxamide (1.0 g) was added, followed by 4-methoxyphenylacetate (1.62 g, 9 mmol) The reaction mixture was refluxed for 16 hours, the solvent was stripped, water was added to the residue, and the product was collected by filtration and recrystallized from ether to afford 0.89 g of 1-cyclopentyl-3-ethyl-6-(4-methoxyphenylmethyl)pyrazolo [3,4-d]pyrimidin-4-one, m.p. 172–173° C.

EXAMPLE 7

To a solution of 1-cyclopentyl-3-ethyl-6-(4-methoxyphenyl methyl)pyrazolo[3,4-d]pyrimidin-4-one (1.0 g, 2.8 mmol) in DMF (25 ml) was added 97% NaH (264 mg), followed 20 minutes later by propanethiol (0.65 g). The reaction mixture was stirred at room temperature for 0.5 hours, then was heated on a steam bath for 20 hours and finally was heated in an oil bath at 120° C. for 8 hours. Additional 97% NaH (264 mg) and propanethiol (0.77 ml) were added and the reaction mixture was heated at 130° C. for 32 hours. The reaction mixture was added to ice water, acetic acid was added and the precipitate which formed was collected by filtration and dried to afford, after recrystallization from ethyl acetate, 0.69 g of 1-cyclopentyl-3-ethyl-6-(4-hydroxyphenylmethyl)pyrazolo[3,4-d]pyrimidin-4-one, m.p. 264–267° C. (dec.).

EXAMPLE 8

(a)

A solution of methyl 4-hydroxyphenylacetate (10 g, 0.06 mol) in DMF (100 ml) was added to 97% NaH (1.78 g, 0.072 mol) in DMF (60 ml) in an ice bath. The reaction mixture was stirred for 0.5 hours and then chloroacetonitrile (5.44 g, 0.072 mol) in DMF (50 ml) was added. The reaction mixture was stirred at room temperature for about 2 days, the solvent was removed in vacuo, and the residue was partitioned between water and ether. The organic layer was separated, washed with saturated $Na_2CO_3$ and then brine, and then was dried over $MgSO_4$, filtered and concentrated in vacuo to afford 12.2 g of methyl 4-(cyanomethoxylphenylacetate.

(b)

Sodium spheres (600 mg) were dissolved in ethanol (15 ml) and 1-cyclopentyl-3-ethyl-5-amino-1H-pyrazole-4-carboxamide (1.0 g) was added, followed by 4-(cyanomethoxy)phenylacetate (1.85 g). The reaction mixture was refluxed overnight, the solvent was stripped and water was added. The reaction mixture was filtered, the filtrate was acidified with 2N HCl and the product was collected by filtration and recrystallized from ethyl acetate to afford 1-cyclopentyl-3-ethyl-6-[4-(carboxymethoxy) phenylmethyl]pyrazolo[3,4-d]pyrimidin-4-one, m.p. 218–220° C.

EXAMPLE 9

Sodium metal (310 mg) was dissolved in ethanol (75 ml) and then 1-cyclopentyl-3-ethyl-5-amino-1H-pyrazole-4-carboxamide (1.1 g, 5 mmol) and methyl 2-pyridinylacetate (1.52 g, 10 mmol) were added. The reaction mixture was heated at reflux for 28 hours, the solvent was removed in vacuo and the residue was dissolved in water (50 ml) and acidified with acetic acid. The mixture was extracted with $CHCl_3$ (100 ml), the solvent was removed and the oily residue was crystallized from cyclohexane to afford 0.85 g of crude product. The product was purified by column chromatography on silica gel eluting with ether, followed by recrystallization from cyclohexane, to afford 1-cyclopentyl-3-ethyl-6-(2-pyridinylmethyl) pyrazolo[3,4-d]pyrimidin-4-one, as yellow crystals, m.p. 120–122° C.

EXAMPLE 10

(a)

97% NaH (3.56 g, 0.14 mol) was suspended in DMF (100 ml) and methyl 4-hydroxyphenylacetate (10 g, 0.06 mol) was added. The reaction mixture was stirred for 0.5 hours, then N-(2-chloroethyl)morpholine hydrochloride (11.2 g) was added and the reaction mixture was stirred at room temperature for about 2 days, and then was heated on a steam bath for 2 hours. The reaction mixture was cooled, filtered and the filtrate was stripped. The residue was partitioned between water and ether, the layers were separated and the aqueous layer was extracted with ether. The organic layers were combined, washed with brine, and dried over $MgSO_4$, filtered and concentrated to afford 11.59 g (69%) of methyl 4-[2-(4-morpholinyl)ethoxy]phenylacetate.

(b)

Sodium (414 mg) was dissolved in ethanol (30 ml) and 1-cyclopentyl-3-ethyl-5-amino-1H-pyrazole-4-carboxamide (2.0 g) and methyl 4-[2-(4-morpholinyl)ethoxy] phenylacetate (5.03 g, 18 mmol) were added. The reaction mixture was refluxed overnight, the solvent was stripped, water was added to the residue, followed by sufficient acetic acid to adjust the pH to 8–9. An oil separated which was collected by decantation and treated with water and saturated $NaHCO_3$. The mixture was extracted with ethyl acetate and washed with water and then saturated $NaHCO_3$ (2×). The aqueous layer was extracted with additional ethyl acetate and the combined organic layers were washed with 2N NaOH and brine. The organic layer was dried over $MgSO_4$, filtered and stripped to afford crude product which was digested with ether and collected by filtration. The crude product was purified by several acid/base work-ups, followed by recrystallization from ether to afford 1.67 g of 1-cyclopentyl-3-ethyl-6-[4-[2-(4-morpholinyl)ethoxy] phenylmethyl]pyrazolo[3,4-d]pyrimidin-4-one, m.p. 136–137° C.

EXAMPLE 11

(a)

A mixture of methyl 4-(cyanomethoxy)phenylacetate (2.5 g, 12 mmol), $NaN_3$ (0.87 g), $NH_4Cl$ (0.72 g, 13 mmol) and DMF (20 ml) was heated at 125° C. for 24 hours. The reaction mixture was cooled, water was added and the mixture was stripped in vacuo without allowing the solution to be stripped to dryness. This procedure was repeated (2×) and then water was added, followed by 2N HCl. The product crystallized from the solution and was collected by filtration, and washed with water and air dried to afford 1.7 g (60%) of methyl 4-(5-tetrazolylmethoxy)phenylacetate.

(b)

Sodium (0.253 g) was dissolved in ethanol (15 ml) and then 1-cyclopentyl-3-ethyl-5-amino-1H-pyrazole-4-carboxamide (0.813 g, 3.7 mmol) and methyl 4-(5-tetrazolylmethoxy)phenylacetate (17 g, 7.3 mmol) were added. The reaction mixture was refluxed for about 2 days, cooled, and then the solvent was removed in vacuo. The residue was treated with water and acetic acid and the precipitate which formed was collected by filtration and dried at 60° C. under vacuum. The product was then dissolved in ethyl acetate, extracted with $Na_2CO_3$ (4×200 ml) and the aqueous layer was acidified to pH 2.5 with concentrated HCl. The aqueous layer was then extracted with ethyl acetate (2×300 ml) and the organic layer was dried over $MgSO_4$, filtered and concentrated in vacuo. The solid residue was recrystallized from ethyl acetate to afford 0.21 g of 1-cyclopentyl-3-ethyl-6-[4-(5-tetrazolylmethoxy) phenylmethyl]pyrazolo[3,4-d]pyrimidin-4-one.2/5 hydrate, m.p. 240–242° C.

EXAMPLE 12

(a)

A suspension of 97% NaH (3.0 g, 0.12 mol) in DMF (100 mL) was stirred for 0.5 hours, then benzimidazole (11.8 g, 0.1 mol) in DMF (50 mL) was added over 30 minutes, followed by ethyl bromoacetate (20 g, 0.12 mol) in DMF (50 mL). The reaction mixture was stirred at room temperature overnight, $NH_4Cl$ was added, and the reaction mixture was stipped. Water was added to the residue, and it was extracted with $CH_2Cl_2$ (3×200 mL). The organic layer was dried over $MgSO_4$, filtered and concentrated in vacuo. The residue was treated with ethyl acetate, a white solid was collected by filtration and the filtrate was concentrated in vacuo and the residue was recrystallized from water to afford 8.0 g of 1-(ethoxycarbonylmethyl)benzimidazole, m.p. 63–64° C.

(b)

Sodium (338 mg) was dissolved in ethanol (30 mL) and 1-(ethoxycarbonylmethyl)benzimidazole (3.0 g, 14.7 mmol) and 1-cyclopentyl-3-ethyl-5-amino-1H-pyrazole-4-carboxamide (1.6 g) were added. The reaction mixture was refluxed overnight, the solvent was stripped and the residue was treated with water and acetic acid. A precipitate formed which was collected by filtration and washed with water to afford 1.96 g (75%) of 1-cyclopentyl-3-ethyl-6-[1-benzimidazolylmethyl]pyrazolo-[3,4-d]pyrimidin-4-one, m.p. 256–259° C.

EXAMPLE 13

Sodium (0.11 g) was dissolved in ethanol and then 1-cyclopentyl-3-ethyl-5-amino-1H-pyrazole-4-carboxamide (0.49 g, 2.21 mmol) was added, followed 10 minutes later by ethyl 3-pyridinylacetate (0.73 g) in ethanol (2 mL). The reaction mixture was refluxed overnight, additional 3-pyridinylacetate (0.35 g) was added and the reaction mixture was again refluxed overnight. The reaction mixture was cooled to room temperature, the solvent was stripped and the residue was dissolved in water and treated with acetic acid (to pH of 7). The mixture was extracted with $CHCl_3$ (3×50 mL), the organic layers were combined, dried over $MgSO_4$ and stripped to a pale yellow oil. The oil was crystallized by the addition of ether and the product was collected by filtration and washed with ether to afford 0.4 g of 1-cyclopentyl-3-ethyl-6-[3-pyridinylmethyl]pyrazolo[3,4-d]pyrimidin-4-one.

EXAMPLE 14

To a suspension of 1-cyclopentyl-3-ethyl-6-[4-hydroxy phenylmethyl]pyrazolo[3,4-d]pyrimidin-4-one (2.68 g, 7.9 mmol) and 40% dimethylamine (5 mL) in acetic acid (50 mL) was added 37% formaldehyde (5 mL). The reaction mixture was stirred at room temperature for 2 hours, then was heated on a steam bath at 100° C. for 4 hours. The solvent was stripped, ethanol was added to the residue and the ethanol was stripped. The residue was purified by preparative thin layer chromatography eluting with 5% isopropylamine/ethyl acetate to afford, after recrystallization from ether, 0.79 g of 1-cyclopentyl-3-ethyl-6-[3,5-dimethylamino-4-hydroxyphenylmethyl]pyrazolo[3,4-d] pyrimidin-4-one, m.p. 164–166° C.

EXAMPLE 15

(a)
A solution of ethyl bromoacetate (20.9 g) in acetonitrile (30 mL) was added to a mixture of $K_2CO_3$ (27.6 g, 0.2 mol) and 1,2,3,4-tetrahydro-2-isoquinoline (13.3 g, 0.1 mol) in acetonitrile (220 mL). The reaction mixture was stirred at room temperature for about 2 days, and then was refluxed for 4 hours. The reaction mixture was filtered, the filtrate was concentrated in vacuo and the residue was partitoned between ether and water. The ether layer was separated, dried over $MgSO_4$ and concentrated in vacuo to afford a liquid which was dissolved in ether (200 mL), cooled and treated with $Et_2O \cdot HCl$ to afford 12,5 g (77%) of ethyl 1,2,3,4-tetrahydro-2-isoquinolinylacetate hydrochloride.
(b)
Ethyl 1,2,3,4-tetrahydro-2-isoquinolinylacetate-hydrochloride (3.63 g) was dissolved in water (100 mL), treated with $NaHCO3$ and then extracted with ether (3×75 mL). The combined organic layers were dried over $MgSO_4$, filtered and stripped to afford 3.02 g of ethyl 1,2,3,4-tetrahydro-2-isoquinolinylacetate as a pale yellow liquid.
(c)
Sodium (0.24 g) was dissolved in ethanol (25 mL) and 1-cyclopentyl-3-ethyl-5-amino-1H-pyrazole-4-carboxamide (1.09 g, 4.91 mmol) followed by ethyl 1,2,3,4-tetrahydro-2-isoquinolinyl acetate (2.15 g) were added. The reaction mixture was refluxed for about 2 days, the solvent was stripped and the residue was treated with water and acetic acid. A gum formed which was extracted with $CHCl_3$ (3×100 mL) and the organic layers were combined, dried over $MgSO_4$, filtered and stripped to afford a yellow solid which was washed with ether to afford (0.6 g) of crude product. The crude product was combined with the crude product from a similar experimental run and the mixture was purified by column chromatography on silica gel eluting with ethyl acetate/hexane (1/1). Additional product was also obtained from concentration of the above ether filtrate and purification by column chromatography as described above. The product fractions were pooled and recrystallized from ether to afford 1-cyclopentyl-3-ethyl-6-(1,2,3,4-tetrahydro-2-isoquinolinylmethyl)pyrazolo[3,4-d]pyrimidin-4-one, as a white solid, m.p. 149–151° C.

EXAMPLE 16

(a)
Ethyl bromoacetate (8.4 mL) was added dropwise to a stirred mixture of $K_2CO_3$ (20.7 g, 150 mmol) and 1,2,3,4-tetrahydro-1-quinoline (10.0 g, 75.08 mmol) in acetonitrile (150 mL) and the reacton mixture was stirred at room temperature for 48 hours. The reaction mixture was filtered, the filtrate was concentrated in vacuo, and the residue was partitioned between ether and water. The organic layer was separated, washed with brine, dried over $MgSO_4$ and evaporated to give 15.0 g (91%) of ethyl 1,2,3,4-tetrahydro-1-quinolinylacetate, as an amber liquid.
(b)
Sodium (0.33 g) was dissolved in ethanol (30 mL) and 1-cyclopentyl-3-ethyl-5-amino-1H-pyrazole-4-carboxamide (1.54 g, 6.94 mmol) followed by ethyl 1,2,3,4-tetrahydro-1-quinolinylacetate (3.04 g) in ethanol (5–10 mL) were added. The reaction mixture was heated to reflux for about two days, the solvent was stripped and the resulting oil was treated with water and neutralized with acetic acid. A precipitate formed which was extracted with $CHCl_3$, dried over $MgSO_4$ and stipped to afford an amber oil. The oil was purified by column chromatography on silica gel elutuing with ethyl acetate/hexane (1/1), followed by recrystallization from acetonitrile to afford 1-cyclopentyl-3-ethyl-6-(1,2,3,4-tetrahydro-1-quinolinylmethyl)pyrazolo[3,4-d] pyrimidin-4-one, as a white crystalline solid.

EXAMPLE 17

Sodium (0.68 g) was dissolved in ethanol and 1-cyclopentyl-3-ethyl-5-amino-1H-pyrazole-4-carboxamide (3.0 g, 13.5 mmol), followed by ethyl glycolate (2.8 g, 27 mmol) were added. The reaction mixture was refluxed overnight, the ethanol was stripped and water, followed by 2N HCl were added to the residue. A precipitate formed which was collected by filtration, washed with saturated $NaHCO_3$, and then water. The product was recrystallized from ethyl acetate, then ether to afford 0.83 g of 1-cyclopentyl-3-ethyl-6-(hydroxymethyl)pyrazolo[3,4-d] pyrimidin-4-one, m.p. 183–184° C.

EXAMPLE 18

(a)
To a mixture of 1-cyclopentyl-3-ethyl-6-(hydroxymethyl) pyrazolo[3,4-d]pyrimidin-4-one (1.0 g, 3.8 mmol), $CH_2Cl_2$ (25 mL) and triethylamine (0.77 g, 7.6 mmol) at −50° C. was added methanesulfonyl chloride (0.44 g, 3.8 mmol) in $CH_2Cl_2$ (5 mL). The reaction mixture was stirred for 1 hour, $CH_2Cl_2$ and water were added and the organic layer was separated, dried over $MgSO_4$, filtered and concentrated in vacuo to afford 1.28 g of crude product. The crude product was combined with that from a similar experimental run and the mixture was recrystallized from ether (2×) to afford 1-cyclopentyl-3-ethyl-6-(methylsulfonyloxymethyl) pyrazolo[3,4-d]pyrimidin-4-one, m.p. 138–140° C.
(b)
A mixture of 1-cyclopentyl-3-ethyl-6-(methylsulfonyloxy methyl)pyrazolo[3,4-d]pyrimidin-4-one (1.8 g, 15.3 mmol), 1-(methylcarbonyl)imidazole (640 mg, 5.8 mmol) and $CH_3CN$ (36 mL) was heated at reflux for 6 hours. The solvent was stripped, ice water and saturated $NaHCO_3$ were added and the mixture was extracted with ethyl acetate, dried over MgSO$_4$, filtered and stripped. The product was combined with that from a similar experimental run and the mixture was recrystallized from ethyl acetate. The product was then treated with 2N HCl, extracted with ethyl acetate and the aqueous layer was neutralized with NaHCO$_3$, extracted with ethyl acetate, dried over MgSO$_4$, filtered and stripped. The residue was recrystallized from ethyl acetate to afford 0.54 g of 1-cyclopentyl-3-ethyl-6-(1-imidazolylmethyl)pyrazolo[3,4-d]pyrimidin-4-one, m.p. 252–253° C.

EXAMPLE 19

Sodium (1.19 g) was dissolved in ethanol (85 mL) and 1-cyclopentyl-3-ethyl-5-amino-1H-pyrazole-4-carboxamide (5.7 g, 26 mmol) and then ethyl 3-methoxyphenylacetate (10 g) were added. The reaction mixture was refluxed overnight, cooled to room temperature and the solvent was stripped. Water was added to the residue, followed by 2N HCl and the precipitate which formed was collected by filtration and recrystallized from ethyl acetate to afford 5.08 g of 1-cyclopentyl-3-ethyl-6-(3-methoxyphenylmethyl)pyrazolo[3,4-d]pyrimidin-4-one, m.p. 148–150° C.

EXAMPLE 20

To a solution of 1-cyclopentyl-3-ethyl-6-(3-methoxyphenyl methyl)pyrazolo[3,4-d]pyrimidin-4-one (4.49 g, 13 mmol) in DMF (123 mL) was added 97% NaH (1.26 g), followed 20 minutes later by propanethiol (2.96 g, 39 mmol). The reaction mixture was heated at 130° C. overnight, cooled to room temperature and then ice water, followed by acetic acid were added. A precipitate formed which was collected by filtration, recrystallized from ether and dried at 110° C. and 2 mm Hg to afford 2.72 g of 1-cyclopentyl-3-ethyl-6-(3-hydroxyphenylmethyl)pyrazolo[3,4-d]pyrimidin-4-one, m.p. 195–197° C.

EXAMPLE 21

(a)

A mixture of 3-hydroxyphenylacetic acid (10 g, 66 mmol), ethanolic HCl (160 mL) and H$_2$SO$_4$ (1 mL) was refluxed overnight. The solvent was stripped to afford 11.66 g (98%) of ethyl 3-hydroxyphenylacetate.

(b)

A suspension of 97% NaH (1.75 g, 0.07 mol) in DMF (50 mL) was stirred for 15 minutes then ethyl 3-hydoxyphenylacetate (5.4 g, 0.03 mol) in DMF (25 mL) was added. The reaction mixture was stirred for 0.5 hours, then was cooled in an ice bath and N-(2-chloroethyl)morpholine hydrochloride (5.6 g, 0.03 mol) was added. The reaction mixture was at room temperature overnight, then was heated on a steam bath for four hours. The solvent was stripped, the residue was partitioned between cold water and ether, the organic layer was separated, and the aqueous layer was extracted with ether. The organic layers were combined, dried over MgSO$_4$, filtered and stripped to afford crude product which was purified by column chromatography on silica gel eluting with ethyl acetate to afford 4.64 g of ethyl 3-[2-(4-morpholinyl)ethoxy]phenylacetate.

(c)

Sodium (364 mg) was dissolved in ethanol (30 mL) and then 1-cyclopentyl-3-ethyl-5-amino-1H-pyrazole-4-carboxamide (1.75 g), followed by ethyl 3-[2-(4-morpholinyl)ethoxy]phenylacetate (4.64 g) in ethanol (7 mL) were added. The reaction mixture was refluxed for about 2 days, the solvent was stripped and water, followed by acetic acid were added to the resulting residue. The mixture was treated with NaHCO$_3$, extracted with ethyl acetate (2×300 mL) and the organic layers were combined and washed with saturated Na$_2$CO$_3$, then brine. The organic layer was then dried over MgSO$_4$, filtered and stripped to afford 2.89 g of crude product. The crude product was purified by column chromatography on silica gel eluting with ethyl acetate, followed by recrystallization from ether to afford, after drying at 75° C. and 0.2 mm Hg, 1.21 g of 1-cyclopentyl-3-ethyl-6-[3-[2-(4-morpholinyl)ethoxy]phenylmethyl]pyrazolo[3,4-d]pyrimidin-4-one.

EXAMPLE 22

Sodium spheres (1.0 g, 43.5 mmol) were dissolved in ethanol (50 mL) at reflux and then 1-cyclopentyl-3-ethyl-5-amino-1H-pyrazole-4-carboxamide (2.2 g, 10 mmol), followed by methyl 1-methylpyrrole-2-acetate (3.06 g, 20 mmol) in ethanol (30 mL) were added. The reaction mixture was refluxed under argon overnight, cooled to room temperature and evaporated to dryness. The residue was dissolved in water, the solution was cooled and the resulting solid was collected by filtration to afford recovered starting material. The filtrate was chilled, a solid formed which was collected by filtration, slurried with water and acidified with 2N HCl. The mixture was cooled and the product was collected by filtration and dried at 110° C. in vacuo to afford 1.2 g of 1-cyclopentyl-3-ethyl-6-(1-methyl-2-pyrrolylmethyl)pyrazolo[3,4-d]pyrimidin-4-one, m.p. 214.5–216.5° C. Additional product (0.6 g) was also obtained by acidifying the filtrate with acetic acid, collecting the product by filtration and recrystallizing it from ethyl acetate.

EXAMPLE 23

(a)

A solution of 1-cyclopentyl-3-ethyl-6-(hydroxymethyl)pyrazolo[3,4-d]pyrimidin-4-one (5.15 g) in CH$_2$Cl$_2$ (120 mL) was cooled to −50° C. and triethylamine (4.7 mL), followed by methanesulfonyl chloride (2.09 g, 18 mmol) in CH$_2$Cl$_2$ (24 mL) were added. The reaction mixture was warmed to room temperature and stirred for 3 hours. Water and CH$_2$Cl$_2$ were added to the reaction mixture, the layers were separated and the aqueous layer was extracted with CH$_2$Cl$_2$. The organic layers were combined, dried over MgSO$_4$, filtered and stripped. The residue was taken up in ether, an oil separated which was decanted off and the filtrate was treated with charcoal, filtered and concentrated in vacuo. The residue was recrystallized from ether and dried at 75° C. and 0.2 mm Hg to afford 1.58 g of 1-cyclopentyl-3-ethyl-4-methylsulfonyloxy-6-(methyl sulfonyloxymethyl) pyrazolo[3,4-d]pyrimidine, m.p. 114–116° C.

(c)

97% NaH (0.158 g) was stirred in DMF (25 mL) for 15 minutes, then pyrazole (0.372 g, 58 mmol), followed by 1-cyclopentyl-3-ethyl-4-methylsulfonyloxy-6-(methylsulfonyloxymethyl) pyrazolo[3,4-d]pyrimidine (1.22 g, 2.9 mmol) were added. The reaction mixture was stirred at room temperature for 2 hours, then was heated on a steam bath overnight. Water was added to the reaction mixture, followed by a sufficient amount of 2N HCl to acidify the mixture. The mixture was allowed to stand for 1.5 hours, then the product was collected by filtration and washed with water. The product was purified by preparative thin layer chromatography on silica gel eluting with 50% ethyl acetate/hexane, followed by recrystallization from ether to afford, after drying at 75° C. and 0.2 mm Hg, 0.26 g of 1-cyclopentyl-3-ethyl-6-(1-pyrazolylmethyl)pyrazolo[3,4-d]pyrimidin-4-one, m.p. 130–131° C.

EXAMPLE 24

(a)

A mixture of 4-trifluoromethylphenylacetic acid (15 g), ethanolic HCl (200 mL) and $H_2SO_4$ (1 mL) was refluxed overnight. The solvent was stripped, the residue was partitioned between ethyl acetate and saturated $NaHCO_3$, and then the organic layer was separated, washed with brine, dried over $MgSO_4$, filtered and concentrated to afford 15.35 g (90%) of ethyl 4-trifluoromethylphenylacetate.

(b)

Sodium (622 mg) was dissolved in ethanol (45 mL) and then 1-cyclopentyl-3-ethyl-5-amino-1H-pyrazole-4-carboxamide (3.0 g, 13.5 mmol), followed by ethyl 4-trifluoromethylphenylacetate (6.27 g, 27 mmol) were added. The reaction mixture was refluxed overnight, cooled to room temperature, and the solvent was stripped. Water, followed by 2N HCl were added to the residue and the product was collected by filtration, recrystallized from ether and dried at 110° C. and 0.2 mm Hg to afford 3.03 g of 1-cyclopentyl-3-ethyl-6-(4-trifluoromethylphenylmethyl) pyrazolo[3,4-d]pyrimidin-4-one, m.p. 212–213° C.

EXAMPLE 25

(a) and (b)

To 90% $HNO_3$ (95 mL) at –10 to –15° C. was added 1-cyclopentyl-3-ethyl-6-(phenylmethyl)pyrazolo[3,4-d]pyrimidin-4-one (9.62 g, 30 mmol). The reaction mixture was stirred as such for 1.5 hours, and then was poured into ice water. A precipitate formed which was collected by filtration, recrystallized from ethyl acetate and dried at 100° C. and 0.2 mm Hg to afford 2.31 g of 1-cyclopentyl-3-ethyl-6-(4-nitrophenylmethyl)pyrazolo[3,4-d]pyrimidin-4-one, m.p. 221–223° C. [labelled as Example 25 (a)]. The mother liquors were combined and concentrated in vacuo to afford a mixture of 1-cyclopentyl-3-ethyl-6-(2-nitrophenylmethyl) pyrazolo [3,4-d]pyrimidin-4-one and 1-cyclopentyl-3-ethyl-6-(3-nitrophenyl methyl)pyrazolo[3,4-d]pyrimidin-4-one [labelled as Example 25 (b)].

EXAMPLE 26

1-Cyclopentyl-3-ethyl-6-(4nitrophenylmethyl)pyrazolo[3,4-d]pyrimidin-4-one (2.12 g, 5.8 mmol) in DMF (50 mL) was hydrogenated at 55 psi using 10% palladium on carbon (200 mg) as a catalyst. The reaction mixture was filtered through SUPERCELL®, the filtrate was concentrated in vacuo and the residue was recrystallized from ethyl acetate to afford, after drying at 100° C. and 0.2 mm Hg, 1.28 g of 1-)cyclopentyl-3-ethyl-6-(4-aminophenylmethyl)pyrazolo[3,4-d]pyrimidin-4-one 1/4 hydrate, m.p. 198–199° C.

EXAMPLE 27

(a)

To a solution of 2-hydroxyphenylacetic acid (25 g, 0.16 mol) in DMF (300 mL) was added $K_2CO_3$ (56.7 g, 0.41 mol), followed by methyl iodide (46.7 g, 0.32 mol). The reaction mixture was stirred for about 3 days, filtered and the filtrate was stripped. The residue was taken up in ethyl acetate, washed with water, saturated $Na_2CO_3$, then brine, and then the organic layer was dried over $MgSO_4$, filtered and stripped to afford 26.4 g (92%) of methyl 2-methoxyphenylacetate.

(b)

Sodium (590 mg) was dissolved in ethanol (45 mL) and then 1-cyclopentyl-3-ethyl-5-amino-1H-pyrazole-4-carboxamide (2.65 g, 12 mmol), followed by methyl 2-methoxyphenylacetate (4.7 g, 26 mmol) were added. The reaction mixture was refluxed overnight, the solvent was stripped and the residue was treated with water and then 2N HCl. The product was collected by filtration and recrystallized from ethyl acetate to afford 2.23 g of 1-cyclopentyl-3-ethyl-6-(2-methoxyphenylmethyl)pyrazolo[3,4-d]pyrimidin-4-one, m.p. 145–146° C.

EXAMPLE 28

(a)

A mixture of ethyl 3-acetyl-4-oxopentanoate (37.24 g, 0.2 mol), hydroxylamine hydrochloride (14.6 g, 0.21 mol), NaOAc (17.23 g, 0.21 mol) and ethanol (500 mL) was refluxed for 4 hours. The reaction mixture was filtered, the filtrate was concentrated in vacuo and the residue was heated in acetic acid (12.61 g, 0.21 mol) and toluene (300 mL) for 6 to 6.5 hours with the removal of water. The reaction mixture was filtered and the filtrate was concentrated in vacuo to afford a tan oil which crystallized on cooling. The product was collected by filtration and washed with ether to afford 1.26 g of ethyl 3,5-dimethyl-4-isoxazolylacetate, m.p. 180–182° C. Additional product was obtained by concentration of the ether filtrate and distillation of the residue at 69–81.5° C. and 0.05 mm Hg to afford a total of 31.18 g (85%).

(b)

Sodium spheres (0.23 g) were dissolved in refluxing ethanol (50 mL) and then 1-cyclopentyl-3-ethyl-5-amino-1H-pyrazole-4-carboxamide (1.1 g, 5 mmol), followed by ethyl 3,5-dimethyl-4-isoxazolylacetate (1.83 g, 10 mmol) were added. The reaction mixture was refluxed under argon for 72 hours, acidified with acetic acid and then concentrated in vacuo. The residue was extracted with ether, the ether layer was washed with water, dried over $MgSO_4$, filtered and evaporated to afford, after recrystallization from $CH_3CN$/ether, 0.65 g of 1-cyclopentyl-3-ethyl-6-(3,5-dimethyl-4-isoxazolylmethyl)pyrazolo[3,4-d]pyrimidin-4-one, as a yellow crystalline solid, m.p. 179.5–180° C.

EXAMPLE 29

To a solution of 1-cyclopentyl-3-ethyl-6-(4-aminophenyl methyl)pyrazolo[3,4-d]pyrimidin-4-one (1.3 g, 3.8 mmol) in pyridine (30 mL) cooled in an ice bath was added triethylamine (0.54 mL, 3.8 mmol), followed by methanesulfonyl chloride (0.52 g, 4.6 mmol). The reaction mixture was stirred as such for 3 hours, then at room temperature overnight. Water was added to the reaction mixture and crude product was collected by filtration. The crude product was taken up in ethyl acetate, washed with 2N HCl and the mixture was filtered. The filtrate was dried over $MgSO_4$, filtered and stripped to afford, after recrystallization from ethyl acetate and drying at 110° C. and 0.2 mm Hg, 0.65 g of 1-cyclopentyl-3-ethyl-6-[4-(methylsulfonylamino), phenylmethyl]pyrazolo[3,4-d]pyrimidin-4-one, m.p. 242–243° C.

EXAMPLE 30

A solution of 1-cyclopentyl-3-ethyl-6-(2-methoxyphenyl methyl)pyrazolo[3,4-d]pyrimidin-4-one (1.64 g, 4.6 mmol) in DMF (45 ml) was treated with 97% NaH (0.46 g, 19 mmol), followed by 3-propanethiol (1.08 g, 14 mmol). The reaction mixture was heated at 130° C. overnight and cooled to room temperature. Ice water, followed by acetic acid were added and the product was collected by filtration and washed with water. Recrystallization of the product from ethyl acetate afforded, after drying at 100 ° C. and 0.2 mm Hg, 1.27 g (82%) of 1-cyclopentyl-3-ethyl-6-(2-hydroxyphenylmethyl) pyrazolo[3,4-d]pyrimidin-4-one, m.p. 191–193° C.

EXAMPLE 31

Sodium (414 mg) was dissolved in ethanol (45 ml) and 1-cyclopentyl-3-ethyl-5-amino-1H-pyrazole-4-carboxamide (2 g, 9 mmol), followed by ethyl 3-thienylacetate (3.1 g, 18 mmol) were added. The reaction mixture was refluxed for about 2 days, the solvent was stripped and the residue was treated with water and then dilute HCl. The product was collected by filtration and recrystallized from ethyl acetate to afford, after drying at 100° C. and 0.2 mm Hg, 1.25 g of 1-cyclopentyl-3-ethyl-6-(3-thienylmethyl)pyrazolo[3,4-d]pyrimidin-4-one, m.p. 210–211° C.

EXAMPLE 32

Sodium (414 mg) was dissolved in ethanol (45 ml) and then 1-cyclopentyl-3-ethyl-5-amino-1H-pyrazole-4-carboxamide (2 g, 9 mmol), followed by ethyl 2-thienylacetate (3.1 g, 18 mmol) were added. The reaction mixture was refluxed overnight, cooled to room temperature and the ethanol was stripped. Water, followed by 2N HCl were added to the residue and the product was collected by filtration, and washed with water. The product was recrystallized from ethyl acetate and dried at 90° C. and 0.2 mm Hg to afford 1.19 g of 1-cyclopentyl-3-ethyl-6-(2-thienylmethyl)pyrazolo[3,4-d]pyrimidin-4-one, m.p. 173–174° C.

EXAMPLE 33

(a)

To a solution of 4-chloromethylbenzoic acid (17.1 g, 0.1 mol) in ethanol (200 ml) cooled in an ice bath was added dropwise diethylamine (32.2 g, 0.44 mol) over 20 minutes. The reaction mixture was refluxed for 17 hours, cooled to room temperature and the solvent was stripped. The residue was dissolved in 1N NaOH (50 ml), extracted with ether (50–100 ml) and the aqueous layer was acidified with 2N HCl to a pH of 3. The aqueous layer was stripped and the residue was treated with ethanol, filtered and the ethanol was stripped. The residue was recrystallized from isopropyl alcohol (3×) to afford 13.54 g of 4-diethylaminomethyl benzoic acid hydrochloride, m.p. 189–191° C.

(b)

A mixture of 4-diethylaminomethyl benzoic acid hydrochloride (360 mg, 1.5 mmol), N,N'-carbonyldiimidazole (264 mg, 1.5 mmol) and dioxane (20 ml) was heated on an oil bath for 1 hour. The reaction mixture was cooled to room temperature and 1-cyclopentyl-3-ethyl-6-(4-hydroxyphenylmethyl)pyrazolo[3,4-d]pyrimidin-4-one (500 mg, 105 mmol) and dioxane (10 ml) were added and the reaction mixture was heated at 100° C. overnight. The reaction mixture was cooled, the solvent was stripped and then water and ethyl acetate were added. The ethyl acetate layer was separated, then washed with 2 N HCl (4×150 ml). The aqueous layers were combined, treated with concentrated $NH_4OH$ and then extracted with ethyl acetate (2×). The ethyl acetate layer was washed with brine, dried over $MgSO_4$, filtered and stripped to afford crude product. The crude product was combined with the crude product from a similar experimental run and the mixture was recrystallized from ether to afford 0.46 g of 1-cyclopentyl-3-ethyl-6-[4-[4-(diethylaminomethyl)phenylcarbonyloxy]phenylmethyl] pyrazolo[3,4-d]pyrimidin-4-one, m.p. 143–145° C.

EXAMPLE 34

A mixture of 1-cyclopentyl-3-ethyl-6-(2-nitrophenylmethyl) pyrazolo[3,4-d]pyrimidin-4-one and 1-cyclopentyl-3-ethyl-6-(3-nitrophenylmethyl)pyrazolo[3,4-d]pyrimidin-4-one (7.1 g, 19 mmol) in DMF (300 mL) was hydrogenated at 55 psi in the presence of 10% palladium on carbon (700 mg). The reaction mixture was filtered through SUPERCELL®, and the filtrate was stripped to afford crude product. The crude product was combined with that from two other similar experimental runs and the mixture was recrystallized from ethyl acetate and then chromatographed on silica gel eluting with 50% ethyl acetate/hexane to afford, after recrystallization from ethyl acetate, 1.11 g of 1-cyclopentyl-3-ethyl-6-(2-aminophenyl methyl)pyrazolo[3,4-d]pyrimidin-4-one, m.p. 190–192° C.

EXAMPLE 35

(a)

A mixture of 4-dimethylaminophenylacetic acid (10 g, 56 mmol), ethanolic HCl (160 mL) and concentrated $H_2SO_4$ (1 mL) was refluxed overnight. The solvent was stripped, ethyl acetate and dilute $NH_4OH$ were added to the residue and the layers were separated. The organic layer was washed with brine, dried over $MgSO_4$, filtered and stripped to afford 8.32 g (72%) of ethyl 4-dimethylaminophenyl acetate.

(b)

Sodium (920 mg) was dissolved in ethanol (67 mL) and ethyl 4-dimethylaminophenyl acetate (8.32 g, 40 mmol), then 1-cyclopentyl-3-ethyl-5-amino-1H-pyrazole-4-carboxamide (4.44 g, 20 mmol) were added and the reaction mixture was refluxed for about 2 days. The reaction mixture was cooled to room temperature, the ethanol was stripped and water was added to the residue. The product was collected by filtration, washed with water and recrystallized from ethyl acetate (2×) to afford, after drying at 100° C. and 0.2 mm Hg, 3.41 g of 1-cyclopentyl-3-ethyl-6-(4-dimethylaminophenylmethyl)pyrazolo[3,4-d]pyrimidin-4-one, m.p. 225–226° C.

EXAMPLE 36

(a)

A mixture of 4-(1-imidazolyl)benzaldehyde (5.08 g, 29.5 mmol) and methyl(methylthio)methylsulfoxide (2.57 g, 21 mmol) in THF (5 mL) was treated with a 40% methanolic solution of TRITON® B (3 mL). The reaction mixture was refluxed for 4 hours, additional methyl(methylthio) methylsulfoxide (1.09 g, 8.5 mmol) was added and the reaction mixture was refluxed for an additional 2 hours. The reaction mixture was cooled to room temperature, $CH_2Cl_2$ was added and the organic layer was washed with water, then brine and then was dried over $MgSO_4$, filtered and stripped. The residue was taken up in ethanolic HCl (180 mL) and refluxed for 16 hours. The reaction mixture was cooled, the ethanol was stripped and the residue was treated with water (200 mL) and extracted with ethyl acetate (250 mL). The aqueous layer was treated with dilute $NH_4OH$ and extracted with ethyl acetate (2×) and then the organic layer was washed with brine, dried over $MgSO_4$, filtered and stripped to afford crude product. The crude product was taken up in ethyl acetate, shaken with 25% sodium bisulfite and then brine. The aqueous layer was extracted with ethyl acetate and the combined organic layers were dried over $MgSO_4$, filtered and stripped to afford 1.93 g of ethyl 4-(1-imidazolyl)phenylacetate.

(b)

Sodium (193 mg) was dissolved in ethanol (25 mL) and 1-cyclopentyl-3-ethyl-5-amino-1H-pyrazole-4-carboxamide (0.93 g, 4.2 mmol), followed by ethyl 4-(1-imidazolyl) phenylacetate (1.93 g, 8.4 mmol) in ethanol (7 mL) were added. The reaction mixture was refluxed overnight, the ethanol was stripped and water was added to the residue. The mixture was cooled and the crude product was collected by filtration. The crude product was stirred with 1N HCl and the product was collected by filtration as the hydrochloride salt. The hydrochloride salt was treated with dilute NH$_4$OH, and the resulting precipitate was collected by filtration and recrystallized from ethyl acetate to afford, after drying at 100° C. and 0.2 mm Hg, 0.4 g of 1-cyclopentyl-3-ethyl-6-[4-(1-imidazolyl)phenylmethyl]pyrazolo[3,4-d]pyrimidin-4-one, m.p. 232–234° C.

EXAMPLE 37

(a)

To a mixture of (1-ethoxyethylidene)malononitrile (68 g, 0.5 mol) and tert-butylhydrazine hydrochloride (62.3 g, 0.5 mol) in ethanol (500 mL) was added triethylamine (70 mL, 0.5 mol). The reaction mixture was stirred at room temperature for 2 hours, then was cooled in ice and the product was collected by filtration and washed with ether to afford 85.9 g of 1-tert-butyl-3-methyl-5-amino-1H-pyrazole-4-carbonitrile ⅔ Et$_3$N.HCl. An additional 46.2 g of the desired product was also obtained by concentration of the mother liquor and recrystallization of the residue from ethanol.

(b)

A mixture of 1-tert-butyl-3-methyl-5-amino-1H-pyrazole-4-carbonitrile ⅔ Et$_3$N.HCl (38 g, 0.12 mol) and water (250 mL) was heated at 85° C. The product precipitated from the reaction mixture and was collected by filtration and dried at 90° C. to afford 23.25 g of 1-tert-butyl-3-methyl-5-amino-1H-pyrazole-4-carbonitrile, m.p. 156–157° C.

(c)

To a mixture of water (200 mL), ethanol (120 mL) and KOH (37 g, 0.56 mol) at 0° C. was added 30% H$_2$O$_2$ (89.1 g, 0.786 mol), followed by 1-tert-butyl-3-methyl-5-amino-1H-pyrazole-4-carbonitrile (20.0 g, 0.112 mol). The reaction mixture was stirred for 4 hours and the product was collected by filtration, washed with water and dried to afford 20.64 g (94%) of 1-tert-butyl-3-methyl-5-amino-1H-pyrazole-4-carboxamide, as white needles, m.p. 195–196° C.

(d)

A mixture of 1-tert-butyl-3-methyl-5-amino-1H-pyrazole-4-carboxamide (1.0 g, 5.1 mmol), ethyl phenylacetate (1.67 g, 10.2 mmol), NaOCH$_3$ (1.74 g, 31 mmol) and ethanol (50 mL) was refluxed for about 3 days. The reaction mixture was stripped to dryness and then the residue was treated with water and then acidified with acetic acid. The product was collected by filtration, washed with water and dried to afford 0.53 g (35%) of 1-tert-butyl-3-methyl-6-(phenylmethyl)pyrazolo[3,4-d]pyrimidin-4-one 1/5 hydrate, m.p. 196–197° C.

EXAMPLE 38

(a)

A mixture of 1-cyclopentyl-3-ethyl-5-amino-1H-pyrazole-4-carboxamide (4.6 g, 20.7 mmol), o-ethylxanthic acid potassium salt (6.4 g, 40 mmol) and N-methyl-2-pyrrolidinone (15 mL) was heated at 150–160° C. for 5 hours. The reaction mixture was cooled, water was added and the mixture was filtered. The filtrate was treated with charcoal and then acidified with acetic acid. A precipitate formed which was collected by filtration, washed with water and dried at 90–95° C. to afford 4.7 g of 1-cyclopentyl-3-ethyl-6-(thioxo) pyrazolo[3,4-d]pyrimidin-4-one, m.p.249–251° C.

(b)

A mixture of 1-cyclopentyl-3-ethyl-6-(thioxo) pyrazolo[3,4-d]pyrimidin-4-one (5.2 g, 19.6 mmol), DMF (50 mL) and K$_2$CO$_3$ (2.76 g, 20 mmol) was stirred at ambient temperature for 25 minutes and then dimethyl sulfate (3.88 mL, 40 mmol) was added. The reaction mixture was stirred for 2 hours, then was poured into cold water. The product was collected by filtration, washed with water, recrystallized from cyclohexane/ether and dried at 70–75° C. in vacuo to afford 4.6 g of 1-cyclopentyl-3-ethyl-6-(methylthio) pyrazolo[3,4-d]pyrimidin-4-one, m.p.200–202° C.

Alternatively, the product can be prepared as follows: To a stirred mixture of 1-cyclopentyl-3-ethyl-6-(thioxo) pyrazolo[3,4-d]pyrimidin-4-one (23.4 g, 0.09 mol) in DMF (250 mL) was added NaH (4.0 g, 0.1 mol., 60% dispersion in mineral oil) over 15 minutes. The resulting mixture was cooled in an ice bath, then methyl iodide (6.3 mL, 0.1 mol) was added over 20 minutes and the resulting mixture was stirred for 3 hours. The reaction mixture was poured into water (400 mL) and the precipitate which formed was collected by filtration, washed with water, then hexane and then was dried at 80–85° C. in a vacuum oven to afford 18.6 g (74%) of 1-cyclopentyl-3-ethyl-6-(methylthio)pyrazolo[3,4-d]pyrimidin-4-one, m.p.203–205° C.

(c)

A mixture of 1-cyclopentyl-3-ethyl-6-(methylthio) pyrazolo[3,4-d]pyrimidin-4-one (4 g), CHCl$_3$ (100 mL) and m-chloroperoxybenzoic acid (10.3 g) was stirred overnight. The reaction mixture was extracted with saturated aqueous NaHCO$_3$ (100 mL) and the CHCl$_3$ layer was dried over MgSO$_4$, filtered and concentrated to dryness. The oily residue crystallized on standing and was recrystallized from cyclohexane and dried at 70–75° C. under vacuum to afford 1-cyclopentyl-3-ethyl-6-(methylsulfonyl) pyrazolo[3,4-d] pyrimidin-4-one, m.p.>300° C.

(d)

A mixture of 1-cyclopentyl-3-ethyl-6-(methylsulfonyl) pyrazolo[3,4-d]pyrimidin-4-one (2.3 g, 7.4 mmol) and aniline (1.2 g, 13 mmol) was heated at 180–190° C. for 3 hours. The reaction mixture was cooled to room temperature and allowed to stand at room temperature overnight. Ether was added to the reaction mixture and the product was collected by filtration, washed with ether and dried at 80–85° C. in a vacuum oven to afford crude product. The crude product was treated with saturated NaHCO$_3$ (25 mL) and the insoluble material was collected by filtration, dissolved in hot isopropanol, treated with charcoal and concentrated in vacuo. The residue was crystallized from ether and dried at 80–85° C. in a vacuum oven to afford 0.58 g (25%) of 1-cyclopentyl-3-ethyl-6-(phenylamino)pyrazolo[3,4-d] pyrimidin-4-one.

EXAMPLE 39

A mixture of 1-cyclopentyl-3-ethyl-6-(methylsulfonyl) pyrazolo[3,4-d]pyrimidin-4-one (3 g, 9.6 mmol), phenol (6 g, 64 mmol) and NaH (0.5 g, 12.8 mmol, 60% dispersion in mineral oil) was heated at 170–175° C. for 5 hours. The reaction mixture was poured into water (50 mL) and extracted with CHCl$_3$ (100 mL). The CHCl$_3$ layer was concentrated in vacuo and the residue was purified by column chromatography on silica gel eluting with 10% ether/hexane to afford 2.1 g (68%) of 1-cyclopentyl-3-ethyl-6-(phenyloxy) pyrazolo[3,4-d]pyrimidin-4-one, as a white solid, m.p. 175–177° C.

Biological Test Results

In standard biological test procedures, the compounds of Formula I have been found to possess c-GMP-PDE V (formerly named as c-GMP-PDE I) inhibitory activity and are thus useful in the treatment of heart failure and hypertension. The compounds of Formula I, in combination with nitrates, have also been found to be useful in reversing or reducing nitrate-induced tolerance and thus would be further useful in the treatment of angina pectoris, congestive heart disease and myocardial infarction.

Multiple isozymic forms of cyclic nucleotide phosphodiesterase (PDE) have been identified in mammalian cells. These isozymes hydrolyze cyclic adenosine monophosphate (cAMP) and/or cyclic guanosine monophosphate (cGMP) to the presumably biologically inactive 5'-nucleotide phosphates. Elevation of intracellular cGMP in vascular smooth muscle triggers a cascade of events that leads to a reduction in muscle tone while elevations in renal tubule cell cGMP stimulates natriuresis and diuresis. Vascular smooth muscle and renal cells contain a phosphodiesterase isozyme that has a low Km (1 $\mu$M) for the hydrolysis of cGMP. This isozyme has been referred to as the cGMP-PDE or cGMP-PDE V (formerly was named as cGMP-PDE I since it eluted from an anion-exchange sepharose resin in the first peak of PDE activity at a sodium acetate concentration between 150–200 mM). Thus inhibition of the cGMP-PDE isozyme is a viable subcellular mechanism by which increases in cGMP can produce a reduction in total peripheral resistance and a stimulation of natriuresis and diuresis. The development of cGMP-PDE inhibitors represents an approach for the discovery of agents useful for treating heart failure and hypertension. For example, compounds having high inhibitory potency for the cGMP-PDE are expected to lower blood pressure and induce natriuresis and diuresis.

The c-GMP-PDE V inhibitory activity of representative compounds of the invention was demonstrated by the following procedure.

The cGMP-PDE and other PDE isozymes were isolated from cardiovascular tissues (heart and aorta) of various animal species and man by anion-exchange and affinity chromatography as described by Silver et al., Sec. Messeng. Phos. 13:13–25, 1991; PDE activity, in the presence and absence of test compounds was determined essentially as described by Thompson et al., Adv. Cyclic Nucleotide Res. 10:69–92. To determine the potency and selectivity of compounds as PDE inhibitors, compounds are screened for their effect on cyclic nucleotide hydrolysis at 10 $\mu$M. If $\geq$50% inhibition of PDE activity is observed, an IC$_{50}$ value (concentration of compound causing 50% reduction in PDE activity) and corresponding 95% confidence intervals are generated. The IC$_{50}$ values are calculated from concentration-response curves as described by Tallarida and Murray, Manual of Pharmacologic Calculations with Computer Programs, Procedure 8, Graded Dose-response, pp. 14–19, Springer-Verlag, N.Y., 1981.

The following table summarizes the results obtained from the testing of representative compounds of the invention.

| Example No. | Percent Inhibition at Given $\mu$M or IC$_{50}$(nM) cGMP-PDE V |
|---|---|
| 1(b) | 10 |
| 2(b) | 9% (1 $\mu$M) |
| 3(b) | 22 |
| 4(b) | 650 |
| 5 | 310 |
| 6 | 23 |
| 7 | 19 |
| 8(b) | 1200 |
| 9 | 540 |
| 10(b) | 270 |
| 11(b) | 310 |
| 12(b) | 39% (1 $\mu$M) or 17% (0.1 $\mu$M) |
| 13 | 660 |
| 14 | 77% (10 $\mu$M) or 28% (1 $\mu$M) |
| 15(c) | 1770 |
| 16(b) | 90% (10 $\mu$M) or 32% (1 $\mu$M) |
| 17 | 61% (10 $\mu$M) or 20% (1 $\mu$M) |
| 18(b) | 33% (1 $\mu$M) |
| 19 | 33 |
| 20 | 86 |
| 21(c) | 420 |
| 22 | 300 |
| 23(b) | 33% (1 $\mu$M) |
| 24(b) | 180 |
| 25(a) | 76 |
| 26 | 8.7 |
| 27(b) | 73% (1 $\mu$M) or 25% (0.1 $\mu$M) |
| 28(b) | 48% (1 $\mu$M) |
| 29 | 94% (0.1 $\mu$M) or 77% (0.01 $\mu$M) |
| 30 | 73% (1 $\mu$M) or 43% (0.1 $\mu$M) |
| 31 | 30 |
| 32 | 89% (1 $\mu$M) or 58% (0.1 $\mu$M) or 24% (0.01 $\mu$M) |
| 33(b) | 56% (0.1 $\mu$M) |
| 34 | 78% (1 $\mu$M) or 45% (0.1 $\mu$M) |
| 35 | 53% (1 $\mu$M) or 34% (0.1 $\mu$M) |
| 36(b) | 62% (1 $\mu$M) or 26% (0.1 $\mu$M) |
| 37(d) | 78% (1 $\mu$M) or 36% (0.1 $\mu$M) |
| 38(d) | 270 |
| 39 | 74% (1 $\mu$M) or 33% (0.1 $\mu$M) |

The antihypertensive activity of representative compounds of the invention was demonstrated by the following procedure.

Spontaneously hypertensive rats (SHR) were anesthetized with sodium pentobarbital (50 mg/kg, ip) and instrumented with catheters positioned in the inferior vena cava and abdominal aorta for administration of drug and recording of arterial pressure and heart rate, respectively. After a 2 day recovery from surgery, three baseline blood pressure measurements were made at 5 min intervals in conscious SHR. Compounds to be tested or vehicle were then administered intravenously in a dose-dependent manner (0.3–10 mg base/ kg) while arterial pressure was recorded continuously on a polygraph. The mean arterial pressure response was measured 5 minutes after the administration of each dose of the test compound and the next dose given in a cumulative dose fashion. The response to each dose of the test compound was calculated as the difference from the mean of the three baseline measurements.

The following table summarizes the results obtained from the testing of representative compounds of the invention.

| Example No. | SHR iv % change in mean arterial pressure at Given mg/kg or ED$_{25}$ (mg/kg) |
|---|---|
| 1 (b) | −15% (1 mg/kg) or −29% (30 mg/kg) |
| 6 | 8.4 or −30% (10 mg/kg) |
| 7 | 4.6 |
| 10 (b) | −17% (10 mg/kg) |
| 11 (b) | −4% (10 mg/kg) |
| 19 | 11.0 or −21% (10 mg/kg) |
| 20 | 10.1 or −23% (10 mg/kg) |
| 24 (b) | 8% (10 mg/kg) |
| 25 (a) | −5% (10 mg/kg) |

-continued

| Example No. | SHR iv<br>% change in mean arterial pressure<br>at Given mg/kg or $ED_{25}$ (mg/kg) |
|---|---|
| 26 | 4.2 or −46% (10 mg/kg) or<br>−56% (10 mg/kg, po) |
| 33 (b) | 9.3 or −27% (10 mg/kg) |

The activity of representative compounds of the invention in reversing or reducing nitrate-induced tolerance was demonstrated by the following procedure:

Spontaneously hypertensive rats (17–25 weeks of age) were made nitroglycerin tolerant by repeated administration of high doses of nitroglycerin (100 mg/kg, s.c., 3 times/day for 3 consecutive days). To confirm tolerance challenge doses of nitroglycerin were administered intravenously at doses ranging from 1–300 μg/kg and the maximum change in mean arterial pressure (MAP) for each dose was recorded. Groups of tolerant rats were pretreated with the compounds of the invention (tolerant pretreated group) or with vehicle (0.05 N NaOH) (tolerant vehicle pretreated group) intravenously 5–10 minutes prior to administration of challenge doses of nitroglycerin. The administration of challenge doses of nitroglycerin to non-tolerant rats (the non-tolerant group) caused a dose-dependent decrease in MAP of between 10 to 40 mm Hg. The administration of challenge doses of nitroglycerin to the tolerant vehicle pretreated group resulted in a significant reduction of the hypotensive response. The administration of challenge doses of nitroglycerin to tolerant rats which were pretreated with the compounds of the invention (tolerant pretreated group) resulted in varying degrees of restoration of the hypotensive response. The area under the dose-MAP curve was calculated for the non-tolerant group and for the tolerant vehicle pretreated group and the tolerant pretreated group. The percent reversal of nitrate-induced tolerance was calculated as follows:

Percent Reversal=$(AUC_{tol-pretreated}-AUC_{tol-veh})/(AUC_{nontol}-AUC_{tol-veh}) \times 100$ wherein: $AUC_{nontol}$=the area under the dose-MAP curve for the non-tolerant group. $AUC_{tol-veh}$=the area under the dose-MAP curve for the tolerant vehicle pretreated group. $AUC_{tol-pretreated}$=the area under the dose-MAP curve for the tolerant pretreated group.

A percent reversal of 100% or greater reflects complete reversal of nitrate-induced tolerance, whereas a percent reversal of 0% indicates that no reversal of nitrate-induced tolerance occurred. The following table summarizes the results obtained from the testing of representative compounds of the invention.

| Example | Dose (mg/kg) | Percent (%) Reversal of Nitroglycerin-induced Tolerance |
|---|---|---|
| 6 | 1.0 | 69 |
|   | 3.0 | 140 |
| 7 | 0.3 | 46 |
|   | 1.0 | 45 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:
1. A compound of the formula:

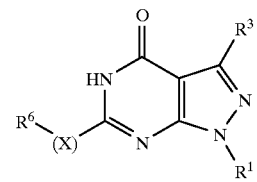

wherein:
 $R^1$ is cyclopentyl;
 $R^3$ is ethyl;
 X is —$CH_2$—; and
 $R^6$ is thienyl, phenyl or phenyl substituted by one or two, the same or different, substituents selected from the group consisting of lower-alkoxy, hydroxy, amino and lower-alkylsulfonylamino, or a pharmaceutically acceptable acid-addition salt and/or hydrate thereof.

2. A compound according to claim 1 selected from the group consisting of:

1-cyclopentyl-3-ethyl-6-(4-methoxyphenylmethyl) pyrazolo [3,4-d]pyrimidin-4-one, 1-cyclopentyl-3-ethyl-6-(4-hydroxyphenylmethyl) pyrazolo[3,4-d]pyrimidin-4-one, 1-cyclopentyl-3-ethyl-6-(phenylmethyl)pyrazolo[3,4-d]pyrimidin-4-one, 1-cyclopentyl-3-ethyl-6-(4-aminophenylmethyl)pyrazolo [3,4-d]pyrimidin-4-one, 1-cyclopentyl-3-ethyl-6-(3,4-dimethoxyphenylmethyl)-pyrazolo[3,4-d]pyrimidin-4-one, 1-cyclopentyl-3-ethyl-6-[4-(methylsulfonamido)-phenylmethyl]pyrazolo[3,4-d]pyrimidin-4-one, and 1-cyclopentyl-3-ethyl-6-(thien-2-ylmethyl)pyrazolo[3,4-d]pyrimidin-4-one.

3. 1-Cyclopentyl-3-ethyl-6-(4-methoxyphenylmethyl) pyrazolo[3,4-d]pyrimidin-4-one, according to claim 2.

4. 1-Cyclopentyl-3-ethyl-6-(4-hydroxyphenylmethyl) pyrazolo[3,4-d]pyrimidin-4-one, according to claim 2.

5. 1-Cyclopentyl-3-ethyl-6-(phenylmethyl)pyrazolo[3,4-d]pyrimidin-4-one, according to claim 2.

6. 1-Cyclopentyl-3-ethyl-6-(4-aminophenylmethyl) pyrazolo[3,4-d]pyrimidin-4-one, according to claim 2.

7. 1-Cyclopentyl-3-ethyl-6-(3,4-dimethoxyphenylmethyl)-pyrazolo[3,4-d]pyrimidin-4-one, according to claim 2.

8. 1-Cyclopentyl-3-ethyl-6-[4-(methylsulfonamido) phenylmethyl]pyrazolo[3,4-d]pyrimidin-4-one, according to claim 2.

9. 1-Cyclopentyl-3-ethyl-6-(thien-3-ylmethyl)pyrazolo[3, 4-d]pyrimidin-4-one, according to claim 2.

10. A pharmaceutical composition which comprises a compound according to claim 1 together with a pharmaceutically acceptable carrier, adjuvant, diluent, or vehicle.

11. A pharmaceutical composition which comprises a compound according to claim 2 together with a pharmaceutically acceptable carrier, adjuvant, diluent, or vehicle.

12. A pharmaceutical composition which comprises a compound according to claim 3 together with a pharmaceutically acceptable carrier, adjuvant, diluent, or vehicle.

13. A pharmaceutical composition which comprises a compound according to claim 4 together with a pharmaceutically acceptable carrier, adjuvant, diluent, or vehicle.

14. A pharmaceutical composition which comprises a compound according to claim 5 together with a pharmaceutically acceptable carrier, adjuvant, diluent, or vehicle.

15. A pharmaceutical composition which comprises a compound according to claim 6 together with a pharmaceutically acceptable carrier, adjuvant, diluent, or vehicle.

16. A method for treating hypertension in a mammalian organism which comprises administering to said organism an effective amount of a compound according to claim 1.

17. A method for treating hypertension in a mammalian organism which comprises administering to said organism an effective amount of a compound according to claim 2.

18. A method for treating hypertension in a mammalian organism which comprises administering to said organism an effective amount of a compound according to claim 3.

19. A method for treating hypertension in a mammalian organism which comprises administering to said organism an effective amount of a compound according to claim 4.

20. A method for treating hypertension in a mammalian organism which comprises administering to said organism an effective amount of a compound according to claim 5.

21. A method for treating hypertension in a mammalian organism which comprises administering to said organism an effective amount of a compound according to claim 6.

* * * * *